(12) United States Patent
Roy et al.

(10) Patent No.: US 7,056,893 B2
(45) Date of Patent: Jun. 6, 2006

(54) TOPICAL TREATMENT FOR PREVENTION OF OCULAR INFECTIONS

(75) Inventors: Samir Roy, San Ramon, CA (US); Lyle M. Bowman, Pleasanton, CA (US)

(73) Assignee: Insite Vision, Inc., Alameda, CA (US)

( * ) Notice: Subject to any disclaimer, the term of this patent is extended or adjusted under 35 U.S.C. 154(b) by 0 days.

(21) Appl. No.: 10/160,060

(22) Filed: Jun. 4, 2002

(65) Prior Publication Data

US 2003/0143259 A1 Jul. 31, 2003

Related U.S. Application Data

(63) Continuation-in-part of application No. 09/767,943, filed on Jan. 24, 2001, now Pat. No. 6,569,443, which is a continuation of application No. 09/346,923, filed on Jul. 2, 1999, now Pat. No. 6,239,113, which is a continuation-in-part of application No. 09/282,165, filed on Mar. 31, 1999, now abandoned.

(51) Int. Cl.
- A61K 31/70 (2006.01)
- A61F 2/00 (2006.01)
- A61F 13/00 (2006.01)

(52) U.S. Cl. ............. 514/29; 424/427; 424/433
(58) Field of Classification Search ............. 514/29; 424/433, 427
See application file for complete search history.

(56) References Cited

U.S. PATENT DOCUMENTS

| | | | |
|---|---|---|---|
| 4,474,768 A * | 10/1984 | Bright .................. | 514/29 |
| 4,512,982 A | 4/1985 | Hauske et al. | |
| 4,517,359 A | 5/1985 | Kobrehel et al. | |
| 4,551,456 A | 11/1985 | Katz | |
| 4,692,454 A | 9/1987 | Mich et al. | |
| 4,851,415 A | 7/1989 | Mich et al. | |
| 5,124,154 A | 6/1992 | Babcock et al. | |
| 5,188,826 A | 2/1993 | Chandrasekaran et al. | |
| 5,192,535 A | 3/1993 | Davis et al. | |
| 5,225,399 A | 7/1993 | Zasloff et al. | |
| 5,239,059 A | 8/1993 | Zasloff et al. | |
| 5,340,572 A | 8/1994 | Patel et al. | |
| 5,424,290 A | 6/1995 | Maloy et al. | |
| 5,441,939 A | 8/1995 | Yang | |
| 5,498,699 A | 3/1996 | Djokic et al. | |
| 5,520,518 A | 5/1996 | Taguchi | |
| 5,538,738 A * | 7/1996 | Ritter et al. .................. | 424/486 |
| 5,578,572 A | 11/1996 | Horwitz et al. | |
| 5,605,889 A | 2/1997 | Curatolo et al. | |
| 5,610,198 A | 3/1997 | Barry, III et al. | |
| 5,631,004 A | 5/1997 | Cagle et al. | |
| 5,679,665 A | 10/1997 | Bergamini et al. | |
| 5,747,058 A | 5/1998 | Tipton et al. | |
| 5,767,153 A | 6/1998 | Bowman et al. | |
| 5,783,561 A | 7/1998 | Horwitz et al. | |
| 5,804,558 A | 9/1998 | Lehrer et al. | |
| 5,807,830 A | 9/1998 | Morozov et al. | |
| 5,814,655 A | 9/1998 | Patel et al. | |
| 5,872,104 A | 2/1999 | Vermeulen et al. | |
| 5,888,973 A | 3/1999 | Lambert, Jr. | |
| 5,912,331 A | 6/1999 | Wilkening | |
| 5,977,171 A | 11/1999 | Bowman et al. | |
| 6,159,458 A | 12/2000 | Bowman et al. | |
| 6,239,113 B1 | 5/2001 | Dawson et al. | |
| 6,265,444 B1 | 7/2001 | Bowman et al. | |
| 6,277,829 B1 * | 8/2001 | Asero et al. .................. | 514/29 |
| 6,309,630 B1 | 10/2001 | Patel et al. | |
| 6,378,526 B1 | 4/2002 | Bowman et al. | |
| 6,397,849 B1 | 6/2002 | Bowman et al. | |
| 6,569,443 B1 * | 5/2003 | Dawson et al. ............. | 424/433 |
| 6,861,411 B1 | 3/2005 | Ahmed | |
| 2003/0171307 A1 | 9/2003 | Boettner | |

FOREIGN PATENT DOCUMENTS

| | | |
|---|---|---|
| EP | 0 126 684 B1 | 11/1984 |
| EP | 0 142 426 | 5/1985 |
| EP | 0 298 650 | 1/1989 |
| EP | 0 391 909 | 10/1990 |
| EP | 0 445 743 A2 | 9/1991 |
| EP | 0 445 743 B1 | 9/1991 |
| EP | 0 467 331 B1 | 1/1992 |
| EP | 0 677 530 B1 | 10/1995 |
| EP | 0 679 400 B1 | 11/1995 |
| EP | 0 711 546 A1 | 5/1996 |
| EP | 0 879 823 A1 | 11/1998 |
| EP | 0 925 789 | 6/1999 |
| EP | 0925 789 A1 | 6/1999 |
| EP | 1075837 A2 | 2/2001 |
| JP | 11-240838 | 9/1999 |
| WO | WO 89/00576 A1 | 1/1989 |
| WO | WO 95/09601 | 4/1995 |
| WO | WO 96 19489 | 6/1996 |
| WO | WO 96 20010 A | 7/1996 |
| WO | WO 96/39995 A1 | 12/1996 |
| WO | WO PCT98/17280 | 4/1998 |

OTHER PUBLICATIONS

Drug Approvals for Jan. 1997, Center for Drug Evaluation and Research, USDA (p. 1, 2; thromax).

Zithromax for IV Infusion Only, Pfizer Labs, New York, NY (2001).

Azithromycin, Official Monographs, USP, vol. 25, pp. 188–190.

Bailey et al., Lancet vol. $3^{rd}$ pp. 453–456 (1993).

(Continued)

*Primary Examiner*—Elli Peselev
(74) *Attorney, Agent, or Firm*—Sughrue Mion, PLLC

(57) ABSTRACT

Azalide antibiotics such as azithromycin are useful in the treatment and prevention of infections by bacteria and other parasites. Stabilized aqueous compositions containing azithromycin suitable for administration without reconstitution are provided for. Also provided for are aqueous formulations suitable for ocular administration in a employing a convenient dosing formulation suitable for administration in depot formats.

44 Claims, 15 Drawing Sheets

OTHER PUBLICATIONS

First Meeting of the WHO Alliance for the Global Elimination of Trachoma, Geneva, Jun. 30–Jul. 1, 1997.

Robert E. Leonard, II et al., *Erythromycin, Clarithromycin, and Azithromycin*, 1997, Textbook of Ocular Pharmacology, pp. 515–523.

Robert H. Cross, et al. *Corneal Pharmacokinetics of Topical Clarithromycin*, Apr. 1995, Investigative Ophthalmology & Visual Science, vol 36, No. 5, pp. 965–968.

A comparison of oral azithromycin with topical oxytetracycline/polymyxin for the treatment of trachoma in children. Abstract XP–002161953 Biosis Information Service, Philadelphia, PA, 1997.

Oral vs. topical erythromycin therapies for chlamydial conjunctivitis. Abstract XP–002161954, Biosis Information Services, Philadelphia, PA, 1982.

Corneal pharmacokinetics of topical clarithromycin. Abstract XP–002161955, Biosis Information Service, Philadelphia, PA, 1995.

Jururatanasirikul, S., et al., *Distribution of azithromycin into brain tissue, cerebrospinal fluid, and aqueous humor of the eye*. Antimicrobial Agents Chemotherapy, 40:825–826(1996).

Thylefors, B. *Azithromycin: A new opportunity for control of trachoma*. WHO Drug Information 10(3):132–133 (1996).

Programme for the Prevention of Blindness and Deafness Alliance for the Global Elimination of Trachoma, "Planning for the Global Elimination of Trachoma (GET) Repport of the WHO Consultation", Geneva, Switzerland (Nov. 25 & 26, 1996).

Programme for the Prevention of Blindness and Deafness Alliance for the Global Elimination of Trachoma, "Report of the First Meeting of the WHO Alliance for the Global Elimination of Trachoma", Geneva, Switzerland (Jun. 30–Jul. 1, 1997).

Programme for the Prevention of Blindness and Deafness, "Report of the Second Meeting of the WHO Alliance for the Global Elination of Trachoma", Geneva, Switzerland (Jan. 12–14, 1998).

Prevention of Blindness and Deafness Geneva, Switzerland, "Report of the Third Meeting of the WHO Alliance for the Global Elimination of Trachoma", Quarzazate, Morocco (Oct. 19–20, 1998).

Dawson et al, A comparison of Oral Azithromycin with Topical Oxytetracycline/Polymyxin for the Treatment of Trachoma in Children, Clinical Infections Diseases 1997:24 (Mar.) 363–368 (full copy).

* cited by examiner

TOPICAL TREATMENT FOR PREVENTION OF OCULAR INFECTIONS

This application is a Continuation-In-Part of U.S. application Ser. No. 09/767,943, filed Jan. 24, 2001; (now U.S. Pat. No. 6,569,443), which is a Continuation of U.S. application Ser. No. 09/346,923, filed Jul. 2, 1999 (now U.S. Pat. No. 6,239,113); which is a Continuation-In-Part of U.S. application Ser. No. 09/282,165, filed Mar. 31, 1999 (now abandoned). The disclosure of each of which is incorporated herein by reference.

FIELD OF THE INVENTION

The present invention relates to a method for treating or preventing infections using stabilized aqueous compositions containing azalide antibiotics, which do not have to be reconstituted prior to use. Azalide antibiotic compositions especially adapted to treat infections of the eye and surrounding tissues are also discussed herein.

BACKGROUND

The eye is susceptible to bacterial and parasitic infections arising from both traumatic and non-traumatic related events. Infections are a concern after ocular surgery, and precautions are correspondingly taken to prevent the onset of infection. However, even without the invasive trauma of a surgical procedure, infections in the eyelids, conjunctiva, cornea, and other ocular tissues can occur.

Treating infections in ocular tissues can be challenging and/or problematic because of the difficulty in delivering an antibiotic to the affected tissue. In general, ocular infections are treated by local injection, systemic administration, or topical application of an antibiotic. The route of administration depends on the antibiotic selected, the location of the infection, and the type of infection.

The simple and direct approach of topically applying the antibiotic to the exterior of the eye has several benefits, including the avoidance of side effects and the reduced chance of developing resistant strains of bacteria as compared to systemic administration. However, for a variety of reasons, many antibiotics are not amenable or suitable for topical application to the eye.

For example, in order for a topical application to be effective, the antibiotic must be able to penetrate the desired tissue. This may include penetrating the conjunctiva and the cornea. Also, the penetration rate must be sufficient to impart an effective dose. Many drugs do not possess a requisite penetration ability with regard to the tissues of the eye. It should be noted that the external layers of the eye are quite different from the tissues encountered in the stomach and intestinal tract. Thus, while a certain drug may be readily absorbed in the intestines and introduced into the blood supply for systemic administration, the same drug may be incapable of being absorbed by or passing through the substantially avascular outer layers of the conjunctiva or cornea at a minimally acceptable therapeutic concentration. The mechanism of transport or uptake of the drug is entirely different for topical administration than for oral administration.

Another concern is that the antibiotic will be toxic to the eye. A toxic response could include redness, swelling or discharge. Toxicity is especially problematic for topical administration because it is a concentration-dependent phenomenon. The concentration ratio between tear fluid and ocular tissue in topical administration is generally in the range of about 1:500 to 1:1000, due to the penetration gradient. Thus, while a drug may be non-toxic at the minimum effective concentration, the 500% to 1000% increase in concentration associated with topical administration may well induce a toxic response. Again, the fact that oral or systemic administration shows the drug to be compatible with ocular tissue does not predict or address the toxicity issue associated with topical administration.

A further potential unsuitability of an antibiotic is the practicality of topical administration by the patient. Assuming that sufficiently high concentrations of the antibiotic can be used to achieve an effective dose within the target tissue without a toxic response, the application may nonetheless be irritating. An irritation response includes temporary burning, stinging and/or watering of the eye. Beyond whether the increased watering of the eyes washes away so much of the antibiotic composition that an effective dose is prevented, the patient may simply be resistant to complying with the dosage regimen because of the irritation. By failing to comply with the dosing regimen, the treatment efficacy is reduced or eliminated.

Some antibiotics have been found to sufficiently meet the above requirements so as to be applicable to topical administration. Examples of antibiotics that are reported to be useful in ocular topical administration include tobramycin, gentamycin, fluoroquinolone derivatives including norfloxacin, ofloxacin, and ciprofloxacin, naphthyridine, tetracyclines, and erythromycin. These antibiotics are typically administered by applying drops every 2 hours for the first two days and every 4 hours for the next several days. While this may be a common dosing regimen employed with aqueous solutions to treat ocular infections, such an extensive dosing regimen is inconvenient, and obtaining patient compliance can be difficult. Of course, the greater the non-compliance with the regimen, the less effective the treatment. In addition, while some antibiotics may meet other requirements for ophthalmic administration, their use is limited by their poor stability in solution. While these antibiotics can be reconstituted prior to use, reconstitution is limited by the ready availability of sterile pyrogen free solvents, the consistency of the reconstituted dosage, and the conditions under which the reconstituted materials can be stored. Reconstitution of marginally stable antibiotics, which are to be applied in repeated doses, is further limited by the time between the reconstitution and the administration of the final dose. It would be beneficial to provide additional antibiotic formulations that are sufficiently stable so that they do not require reconstitution immediately prior to administration. It would further be beneficial if the antibiotic compositions were adaptable to administration via diverse routes such as parenterally, orally and topically, and if the formulations provided high bioavailability of active antibiotic. It would also be desirable if the formulations were capable of effective topical administration of antibiotics to the eye and treatment of infections of the eye and surrounding tissues. It would be further desirable to provide a topical ophthalmic formulations that are effective against a broad spectrum of bacteria and that can be administered in a less extensive regimen.

SUMMARY OF THE INVENTION

The present invention relates to stabilized aqueous formulations of azalide antibiotics. The stabilized formulations do not require reconstitution with separately supplied sterile water, aqueous solutions, or aqueous suspensions. Such stabilized formulations can be administered to a variety of tissues either prophylactically or to treat bacterial or parasitic infections of susceptible organisms. Routes of administration include topical, parenteral, and oral. Parenteral administration may be employed to treat a specific tissue, area of the body, or limb of a patient or parenteral administration may be employed for systemic treatment, for example by intravenous or intralymphatic administration.

The present invention includes and provides an ophthalmic composition comprising water and an azalide antibiotic; wherein said composition has a pH of about 5.0 to about 7.0. The present invention also includes and provides an ophthalmic composition comprising about 0.4% to about 1.0% sodium chloride; about 0.1% to about 2.0% citric acid; about 0.1% to about 2.0% sodium citrate, about 0.1% to about 10.0% azithromycin; and water, wherein said composition has a pH of about 5.0 to about 7.0 or more preferably from a pH of about 6.0 to about 6.5. In a preferred embodiment the composition further comprises a lightly crosslinked carboxyl containing polymer which causes the solution to undergo a rapid increase in viscosity upon a pH rise associated with administration to tissues such as those of the eye and surrounding region.

The present invention also includes and provides a method of preparing a stable azalide antibiotic composition for ophthalmic use, comprising the steps of: (a) combining an azalide antibiotic with citric acid; (b) adding citrate to the solution formed in step (a); (c) adding water to the solution formed in step (b); and (d) adjusting the solution formed in step (c) to a pH of about 5.0 to about 7.0, or more preferably from a pH of about 6.0 to about 6.5. The present invention also includes and provides a method for treating an eye, which comprises applying a composition comprising water and an azalide antibiotic, wherein said composition has a pH of about 5.0 to about 7.0 or more preferably from a pH of about 6.0 to about 6.5.

The present invention further relates to a processes for treating infections of the eye or surrounding tissue that comprises topically applying an azalide antibiotic to an eye in an amount effective to treat or prevent infection in a tissue of the eye. A preferred azalide antibiotic is azithromycin.

A preferred form of the invention involves forming or supplying a depot of the azalide antibiotic in contact with the eye for a sufficient length of time to allow a minimum inhibitory concentration (MIC) of the azalide antibiotic to diffuse into the cells of the targeted eye tissue(s). Once the MIC threshold has been surpassed, a therapeutically effective concentration of the azalide antibiotic will remain in the tissue(s) for a considerable period due to its long half-life. Accordingly, an advantage of certain preferred forms of the present invention is a simplified dosing regimen. For example, one or two topical applications may provide a sufficient tissue concentration that an inhibitory concentration remains resident in the infected tissue for several days, i.e. 4–12 days. Thus, a complete treatment regimen may involve only one or two topical applications.

Depot of the azalide antibiotic can be formed by several means. In one preferred embodiment a depot for topical administration can be formed by including lightly crosslinked carboxyl containing polymers to the formulation, which causes the solution to undergo a rapid increase in viscosity upon a pH rise associated with administration to tissues such as those of the eye and surrounding region. In another embodiment, a depot of the azalide antibiotic can be formed by injection of a bolus of the antibiotic composition into a target tissue. In one preferred method of ophthalmic administration the injection is intended to form a depot of material within the sclera, to accommodate extended release of the material to the surrounding tissues. Methods of intrascleral administration are discussed in U.S. patent application Ser. No. 09/127,920, filed Aug. 3, 1998 now U.S. Pat. No. 6,378,526 and copending U.S. patent application Ser. No. 09/366,072, filed Aug. 2, 1999, now U.S. Pat. No. 6,397,849. Other means of forming depot include the use of inserts loaded with a bolus of the drug to be delivered. Inserts placed under the eyelid have been used for example to deliver therapeutics to the ocular and periocular region.

DETAILED DESCRIPTION OF THE INVENTION

Figure 1:
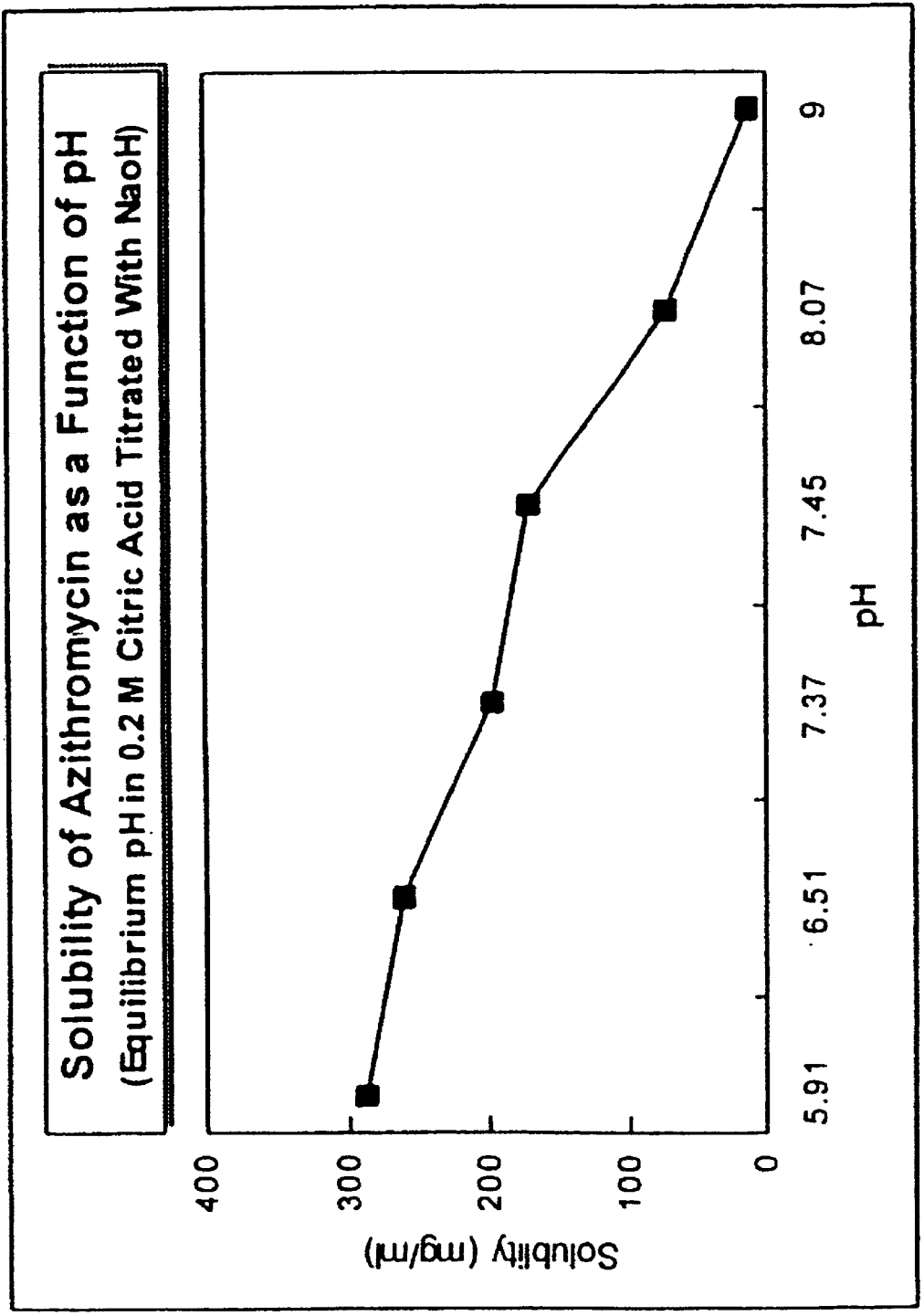
FIG. 1 is a graph depicting the solubility of azithromycin as a function of pH.

Azalides, also occasionally referred to as azolids, are a known subclass of macrolide antibiotics. For the present invention and as used in this specification, an "azalide antibiotic" means a derivitized erythromycin A structure having a nitrogen atom inserted into the lactone ring. Additional variations from the erythromycin structure are also embraced within the term "azalide antibiotic." Such additional variations include the conversion of a hydroxyl group to an alkoxy group, especially methoxy (so-called "O-methylated" forms), for example at the 6 and/or 12 position. Such compounds are described in U.S. Pat. No. 5,250,518. Other variations relate to derivatives of the sugar moieties, for example, 3" desmethoxy derivatives and the formation of oxo or oxime groups on the sugar ring such as at the 4" position as described in U.S. Pat. No. 5,441,939. This patent also teaches that the adjacent hydroxyl groups at the 11 and 12 position of the lactone ring can be replaced with a single carbonate or thiocarbonate group. In short, an azalide antibiotic for purposes of the present invention is any derivative of the erythromycin structure that contains a 15-member lactone ring having a ring nitrogen, preferably at the 9 position, and a sugar group attached via a glycosidic bond to the lactone ring at the 5 position and at the 3 position, and which still exhibits bacteriostatic or bactericidal activity.

Preferred azalide antibiotics are represented by formula (I) and pharmaceutically acceptable salts thereof.

$R^1$ and $R^2$ each independently represent a hydrogen atom or a methyl group.

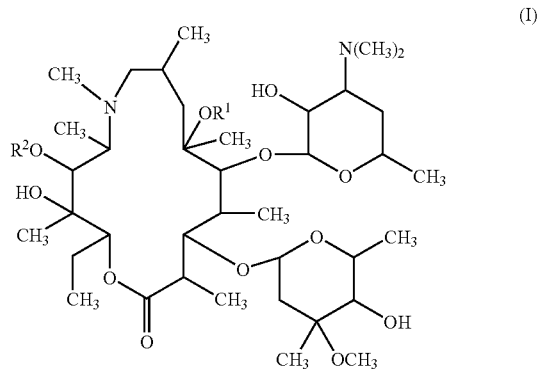

(I)

Preferably at least one of $R^1$ and $R^2$ is a hydrogen atom. Azithromycin, the common name for N-methyl-11-aza-10-deoxo-10-dihydroerythromycin, corresponds to the compound of formula (I) where both $R^1$ and $R^2$ are a hydrogen atom. Azithromycin was disclosed in U.S. Pat. Nos. 4,474,768 and 4,517,359, and is the most preferred azalide antibiotic. In particular, the dihydrate form of azithromycin is especially contemplated for use in the present invention, although other forms are also suitable.

Azithromycin has been used as an oral antibiotic and is sold worldwide under the brand name Zithromax® by Pfizer Inc. Azithromycin is a broad spectrum antibiotic that is generally more effective in vitro than erythromycin. Moreover, because azithromycin is an azalide and thus has a ring nitrogen atom, it exhibits improved acid-stability, half-life, and cellular uptake in comparison to erythromycin. The high uptake and retention of azithromycin into cells, including phagocytic blood cells, allows systemically administered azithromycin to be nonetheless preferentially delivered to the site of the infection. The mechanism has been reported to be as follows. The ingested azithromycin is absorbed through the intestine into the blood stream from which it enters most cells of the body including, inter alia, the white blood cells. In response to an infection within the body, white blood cells, including those containing azithromycin, are attracted to the infectious site. When the white blood cells die, the azithromycin is released. As more and more white blood cells arrive at the infectious site and die, the concentration of azithromycin in the surrounding tissue increases, eventually surpassing the minimum inhibitory concentration (MIC). Once at the infectious site, the azithromycin remains in the tissue for a prolonged period of time, due to its long half-life, such that an effective concentration of azithromycin is present at the infected site for many days after cessation of administration. Azalide antibiotics, while typically administered via the oral route, are amenable to topical and parenteral administration. One of the principal limitations in the use of azalide antibiotics in topical and parenteral formulations has been the lack of stable aqueous formulations amenable to packaging and commercial distribution. In order to overcome the instability of aqueous formulations, reconstitutable preparations of azalide such as ZITHROMAX® (azithromycin for injection, Pfizer Labs NY, N.Y.) have been prepared and marketed. Reconstitutable formulations suffer from several disadvantages including the ready availability of sterile pyrogen free water for reconstitution, the consistency of the reconstituted dosage (which can be affected by both inaccurate delivery of solvent and incomplete dissolution or suspension), and the conditions under which the reconstituted materials can be stored. Moreover, formulations that are to be administered in repeated doses must deliver a therapeutically effective dose of the active component from the first to the last administration. Thus, reconstitution as a means of providing therapeutic materials with a limited stability remains limited by the effective stability of the formulation over the course of treatment.

As an alternative to providing compositions capable of being reconstituted, identification of stable aqueous formulations compatible with administration topically or parenterally offers several advantages. Azithromycin antibiotics have herein been discovered to have a maximum stability over a pH interval of about 5.0 to about 7.0, preferably with a maximum at a pH of about 6.3. In addition the stabilized antibiotic formulations may advantageously contain one or more chelating agents or antioxidants. Stabilized formulations of azalide antibiotics can be prepared over this pH interval under strictly controlled Good Manufacturing Practice (GMP) conditions, insuring both the quality and uniformity of the materials while avoiding the requirement for reconstitution by the pharmacist, physician, or patient. Moreover, sufficiently stable formulations are amendable to commercial transportation and can dispensed and administered without concern that the active component will be unacceptably degraded. In addition, suitably stable formulations can be dispensed for administration over an extended course of treatment, or packaged in single dose forms suitable for direct administration by a patient or physician without the effort or concern over reconstitution. To this end, this disclosure describes stable aqueous formulations of azalide antibiotics amendable to administration topically, parenterally, and orally. In preferred embodiments of this invention, wherein the composition is intended for topical administration to ocular or periocular tissues, the composition may be formulated for application as a liquid drop, ointment, a viscous solution or gel, a ribbon, or a solid. The composition can be topically applied, for example, without limitation, to the front of the eye, under the upper eyelid, on the lower eyelid and in the cul-de-sac.

In an alternative embodiment the stabilized formulation of azalide antibiotic is formulated as a solid, semi-solid, powdered, or lyophilized composition, which upon addition of water or aqueous solutions produces a stabilized azalide formulation having a pH of about 5.0 to about 7.0, more preferably of about 5.8 to about 6.8, more preferably from about 6.0 to about 6.6, more preferably of about 6.2 to about 6.4, more preferably of about 6.25 to 6.35, and even more preferably about 6.3. Solid, semi-solid, powdered, or lyophilized composition may be prepared and packaged for single dose or multiple dose delivery. The solid, semi-solid, powdered, or lyophilized compositions may also contain one or more additional medicaments or pharmaceutically acceptable excipients compatible with the intended route of administration. In a preferred embodiment for ocular administration, the solid, semi-solid, powdered, or lyophilized compositions may also contain polymeric suspending agents. The reconstitutable formulations of stabilized azalide antibiotics of this invention thus provide for compositions having the advantages of a shelf life comparable to that of commercially available azalide antibiotics, and additionally, the extended shelf life of the stablized aqueous formulations described herein.

Although azithromycin can reach many of the tissues and fluids of the eye by oral administration, it has been discovered that azalide antibiotics in general and azithromycin in particular are amenable to topical administration to eye and periocular tissues. U.S. patent application Ser. No. 09/346, 923, filed Jul. 2, 1999, now U.S. Pat. No. 6,239,113. The azalide antibiotic can be supplied to the eye surface in a variety of ways, including as an aqueous ophthalmic solution or suspension, as an ophthalmic ointment, and as an ocular insert, but application is not limited thereto. Any technique and ocular dosage form that supplies an azalide antibiotic to the external eye surface is included within the definition of "topically applying." Although the external surface of the eye is typically the outer layer of the conjunctiva, it is possible that the sclera, cornea, or other ocular tissue could be exposed such as by rotation of the eye or by surgical procedure, and thus be an external surface. For the purposes of this application, periocular tissues are defined as those tissues in contact with the lachrymal secretions, including the inner surface of the eye lid, the tissues of the orbit surrounding the eye, and the tissues and ducts of the lachrymal gland.

The amount of azalide antibiotic topically supplied is effective to treat or prevent infection in a tissue of the eye. This means that the conditions of application result in a retarding or suppression of the infection. Typically at least about $MIC_{50}$ for the targeted bacteria or parasite is delivered to the ocular tissue by the topical application of an effective amount. More concretely, the concentration within the ocular tissue is desired to be at least about 0.25 µg/g, preferably at least about 1 µg/g, and more preferably at least about 10 µg/g. The amount of azalide actually supplied to the external eye surface will almost always be higher than the tissue concentration. This reflects the penetration hold up of the azalide antibiotic by the outer tissue layers of the eye and that penetration is, to some extent, concentration driven. Thus, supplying greater amounts to the exterior will drive more antibiotic into the tissues. Delivery of formulations as a depot will advantageously maintain the concentration of the azalide antibiotic in the affected tissues at or above the $MIC_{50}$ for a period of at least about 2 hours, or more preferably at least about 4 hours, more preferably at least about 8 hours, or more preferably at least about 12 hours.

Where a series of applications are typically employed in a topical administration dosing regimen, it is possible that one or more of the earlier applications will not achieve an effective concentration in the ocular tissue, but that a later application in the regimen will achieve an effective concentration. This is contemplated as being within the scope of topically applying an azalide antibiotic in an effective amount. However, generally a single application, such as consisting of one or two drops, provides a therapeutically effective concentration (e.g. one that retards or suppresses the infection) of the azalide antibiotic within a tissue of the eye. Indeed, although dependent on the amount and form of the ophthalmic composition, a single application will typically provide a therapeutically effective amount of the azalide antibiotic within a tissue of the eye for at least about 2, more preferably about 4, more preferably about 8, more preferably about 12, and more preferably at least about 18 hours. As discussed above, the stabilized azalide antibiotic compositions of this invention may be topically administered to a variety of tissues, including the eye, to provide prophylaxis or treatment of infections. In an alternative embodiment, azithromycin compositions of this invention can be administered parenterally by direct administration to muscle or affected tissues, intravenously or intralymphatically. Formulations of this invention to be administered by injection will generally not include polymeric suspending agents.

One embodiment of this invention provides for administration of azalide antibiotic compositions to tissues of the eye by intrascleral injection as disclosed in U.S. Pat. Nos. 6,397,849 and 6,378,526. Administration by means of intrascleral injection may advantageously be employed to provide antibiotics to the tissues of the posterior segment of the eye. Another embodiment of the invention is a method of intrascleral injection, which comprises injecting into the scleral layer of an eye through a location on the exterior surface of the sclera which overlies retinal tissue an effective amount of a azalide antibiotic. Depending on the injection conditions, the azalide antibiotic will (1) form a depot within the scleral layer and diffuse into the underlying tissue layers such as the choroid and/or retina, (2) be propelled through the scleral layer and into the underlying layers, or (3) a combination of both (1) and (2).

Azalide antibiotic formulations of this invention can be used to treat or prevent a D variety of conditions associated with ocular infection. For example, conditions of the eyelids, including blepharitis, blepharconjunctivies, meibomianitis, acute or chronic hordeolum, chalazion, dacryocystitis, dacryoadenities, and acne rosacea; conditions of the conjunctiva, including conjunctivitis, ophthalmia neonatorum, and trachoma; conditions of the cornea, including corneal ulcers, superficial and interstitial keratitis, keratoconjunctivitis, foreign bodies, and post operative infections; and conditions of the anterior chamber and uvea, including endophthalmitis, infectious uveitis, and post operative infections, are a few of the tissues and conditions that can be treated by topical application of an azalide antibiotic. The prevention of infection includes preoperative treatment prior to surgery as well as other suspected infectious conditions or contact. Examples of prophylaxis situations include treatment prior to surgical procedures such as blepharoplasty, removal of chalazia, tarsorrhapy, procedures for the canualiculi and lacrimal drainage system and other operative procedures involving the lids and lacrimal apparatus; conjunctival surgery including removal of ptyregia, pingueculae and tumors, conjunctival transplantation, traumatic lesions such as cuts, burns and abrasions, and conjunctival flaps; corneal surgery including removal of foreign bodies, keratotomy, and corneal transplants; refractive surgery including photorefractive procedures; glaucoma surgery including filtering blebs; paracentesis of the anterior chamber; iridectomy; cataract surgery; retinal surgery; and procedures involving the extraocular muscles. The prevention of ophthalmia neonatorum is also included.

More generally, azalide antibiotic compositions, and more particularly the stabilized azalide antibiotic compositions of this invention, can be used to treat or prevent infections, including ocular infections caused by a variety of bacteria or parasites, including but not limited to one or more of the following organisms: Staphylococcus including *Staphylococcus aureus* and *Staphylococcus epidermidis*; Streptococcus including *Streptococcus pneumoniae* and *Streptococcus pyogenes* as well as Streptococci of Groups C, F, and G and Viridans group of Streptococci; *Haemophilus influenza* including biotype III (*H. Aegyptius*); *Haemophilus ducreyi*; *Moraxella catarrhalis*; Neisseria including *Neisseria gon-*

*orrhoeae* and *Neisseria meningitidis*; Chlamydia including *Chlamydia trachomatis, Chlamydia psittaci*, and *Chlamydia pneumoniae*; Mycobacterium including *Mycobacterium tuberculosis* and *Mycobacterium avium*-intracellular complex as well as a typical mycobacterium including *M. marinum, M. fortuitm*, and *M. chelonae; Bordetella pertussis; Campylobacter jejuni; Legionella pneumophila; Bacteroides bivius; Clostridium perfringens*; Peptostreptococcus species; *Borrelia burgdorferi; Mycoplasma pneumoniae; Treponema pallidum; Ureaplasma urealyticum*; toxoplasma; malaria; and nosema.

Azalide antibiotic compositions of this invention suitable for topical administration to the eye or periocular tissue may include one or more "ophthalmically acceptable carriers."

Ophthalmic carrier(s) is used in a broad sense and includes any material or composition that can contain and release the azalide antibiotic and that is compatible with the eye. Typically the ophthalmically acceptable carrier is water or an aqueous solution or suspension, but also includes oils such as those used to make ointments and polymer matrices such as used in ocular inserts. Generally, azalide antibiotics are poorly soluble in water and their solubility displays a marked pH dependence as shown in FIG. 1. The stabilized compositions of this invention advantageously employ the increased water solubility of the protonated form of the antibiotic that is compatible with the optimal pH range for azalide antibiotic stability. For example, azithromycin dihydrate has good water solubility on the order of 200–250 mg/ml over a preferred pH range of about 6.0 to about 7.0 or over a more preferred pH range from about 6.1 to about 6.4. Accordingly, stabilized aqueous solution of an azalide antibiotic can be formed and used for topical application. Alternatively, aqueous compositions containing a portion of the azalide antibiotic in suspension may be employed for topical administration. Ointments and solid dosage forms can also be used as delivery compositions as are well known in the art. The concentration of azalide antibiotic present in the ophthalmic composition depends upon the dosage form, the release rate, the dosing regimen, and the location and type of infection. Generally speaking, the concentration is from about 0.05% to about 12.0% although it is possible to prepare and utilize compositions with higher concentrations of azalide antibiotics such as 15%, 20%, 25% or even about 30%. In one embodiment of the invention, the concentration is about 0.01% to about 20.0%. In another embodiment of the invention, the concentration is about 0.1% to about 10.0%. In another embodiment of the invention, the concentration is about 0.5% to about 5.0%. In another embodiment of the invention, the concentration is about 1% to about 10%. In another embodiment of the invention, the concentration is about 10% to about 30.0%. In embodiments having solid dosage forms, the compositions can be about 0.5 to 50% (w/w); however, the compositions are not limited thereto.

The fluid ophthalmic compositions of the present invention suitable for topical administration, including both ointments and suspensions, have a viscosity that is suited for the selected route of administration. A viscosity in the range of from about 1,000 to 30,000 centipoise is useful for a drop. About 30,000 to about 100,000 centipoise is an advantageous viscosity range for ophthalmic administration in ribbon form. The viscosity can be controlled in many ways known to the worker skilled in the art.

The osmotic pressure ($\pi$) of the aqueous composition of this invention is generally from about 10 milliosmolar (mOsM) to about 400 mOsM, more preferably from about 260 to about 340 mOsM. If necessary, the osmotic pressure can be adjusted by using appropriate amounts of physiologically and ophthalmically acceptable salts or excipients. Sodium chloride is preferred to approximate physiologic fluid, and amounts of sodium chloride from about 0.01% to about 1.2% by weight, and preferably from about 0.1% to about 1.10.% by weight, and more preferably about 0.7% to about 1.0% by weight based on the total weight of the composition, are typically used. Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can also be used in addition to or instead of sodium chloride to achieve osmolalities within the above-stated range. Similarly, a sugar such as mannitol, dextrose, sorbitol, glucose and the like can also be used to adjust osmolality.

The solubility of the azalide antibiotics in the aqueous ophthalmic composition of this invention is generally about 200 to about 300 mg per milliliter, as shown in FIG. 1. If necessary, the solubility can be adjusted by using appropriate amounts of a solubilizing agent. Citric acid is preferred to obtain the proper solubility, and amounts of citric acid of about 0.01% to about 5% by weight, preferably about 0.05% to about 0.3.% by weight, and more preferably about 0.1% to about 2.0% by weight based on the total weight of the composition, are typically used. In addition to citric acid, other solubilizing agents, including but not limited to other pharmaceutically acceptable organic acids, and alpha, beta, delta and gamma cyclodextrins may be employed to adjust solubility.

If necessary, free divalent metal ions may be removed from the solution by using appropriate amounts of a chelating agent. EDTA disodium is preferred to remove excess free metal ions, and amounts of citric acid of about 0.01% to about 1% by weight, preferably about 0.05% to about 0.5% by weight, and more preferably about 0.1% to about 0.2% by weight based on the total weight of the composition, are typically used. In addition to EDTA, other chelating agents including phosphonic acids such as Dequest 2060 may also be employed. Useful phosphonic include, but are not limited to diethylene triamine penta(methylenephosphonic acid) and the like which are commercially available from Monsanto under the DEQUEST brand name.

The formulations of this invention may also advantageously employ one or more stabilizing agents including antioxidants. Useful antioxidants include but are not limited to sodium bisulfate, butylated hydroxy toluene (BHT), thiourea, and sodium formaldehyde sulfoxylate.

A preferred form of the present invention for topical ophthalmic administration provides for achieving a sufficiently high tissue concentration of azalide antibiotic with a minimum of doses so that a simple dosing regimen can be used to treat or prevent bacterial or parasitic infections. To this end, a preferred technique involves forming or supplying a depot of azalide antibiotic in contact with the external surface of the eye. A depot refers to a source of azalide antibiotic that is not rapidly removed by tears or other eye clearance mechanisms. This allows for continued, sustained high concentrations of azalide antibiotic to be present in the fluid on the external surface of the eye by a single application. In general, it is believed that absorption and penetration are dependent on both the dissolved drug concentration and the contact duration of the external tissue with the drug-containing fluid. As the drug is removed by clearance of the ocular fluid and/or absorption into the eye tissue, more drug is provided, e.g. dissolved, into the replenished ocular fluid from the depot.

Accordingly, the use of a depot more easily facilitates loading of the ocular tissue in view of the typically slow and low penetration rate of the generally water-insoluble or poorly soluble azalide antibiotics. The depot, which retains a bolus of concentrated drug, can effectively slowly "pump" the azalide antibiotic into the ocular tissue. As the azalide antibiotic penetrates the ocular tissue, it is accumulated therein and not readily removed due to its long half-life. As more azalide antibiotic is "pumped" in, the tissue concentration increases and the minimum inhibitory concentration threshold is eventually reached or exceeded, thereby loading the ocular tissue with azalide antibiotic. By significantly exceeding the $MIC_{50}$, more preferably the $MIC_{90}$ level, provided the toxicity limit is not exceeded, a therapeutically effective concentration will remain active in the tissue for an extended period of time due to the low clearance rate of the azalide antibiotic from the tissue. Thus, depending on the depot, one or two applications may provide a complete dosing regimen. Indeed, such a simple dosing regimen may provide a 6 to 14 day treatment concentration within the ocular tissue. A preferred dosing regimen involves one to two doses per day over a one to three day period, more preferably one or two doses in a single day, to provide in vivo at least a 6 day treatment and more typically a 6 to 14 day treatment.

A depot can take a variety of forms so long as the azalide antibiotic can be provided in sufficient concentration levels therein and is releasable therefrom, and that the depot is not readily removed from the eye. A depot generally remains for at least about 30 minutes after administration, preferably at least 2 hours, and more preferably at least 4 hours. The term "remains" means that neither the depot composition nor the azalide antibiotic is exhausted or cleared from the surface of the eye prior to the indicated time. In some embodiments, the depot can remain for up to eight hours or more. Typical ophthalmic depot forms include aqueous polymeric suspensions, ointments, and solid inserts. Polymeric suspensions are the most preferred form for the present invention and will be discussed subsequently.

Ointments, which are essentially an oil-based delivery vehicle, are a well known compositions for topical administration. Common bases for the preparation of ointments include mineral oil, petrolatum and combinations thereof, but oil bases are not limited thereto. When used for ophthalmic administration, ointments are usually applied as a ribbon onto the lower eyelid. The disadvantage of ointments is that they can be difficult to administer, can be messy, and can be uncomfortable or inconvenient to the patient. Moreover, temporarily blurred vision is a common difficulty encountered when they are employed for ophthalmic administration.

Inserts are another well-known ophthalmic dosage form and comprise a matrix containing the active ingredient. The matrix is typically a polymer, and the active ingredient is generally dispersed therein or bonded to the polymer matrix. The active ingredient is slowly released from the matrix through dissolution or hydrolysis of the covalent bond, etc. In some embodiments, the polymer is bioerodible (soluble) and the dissolution rate thereof can control the release rate of the active ingredient dispersed therein. In another form, the polymer matrix is a biodegradable polymer that breaks down, such as by hydrolysis, to thereby release the active ingredient bonded thereto or dispersed therein. The matrix and active ingredient can be surrounded with a polymeric coating, such as in the sandwich structure of matrix/matrix+ active/matrix, to further control release, as is well known in the art. The kinds of polymers suitable for use as a matrix are well known in the art. The azalide antibiotic can be dispersed into the matrix material or dispersed amongst the monomer composition used to make the matrix material prior to polymerization. The amount of azalide antibiotic is generally from about 0.1 to 50%, more typically about 2 to 20%. The insert can be placed, depending on the location and the mechanism used to hold the insert in position, by either the patient or the doctor, and is generally located under the upper eye lid. A variety of shapes and anchoring configurations are recognized in the art. Preferably a biodegradable or bioerodible polymer matrix is used so that the spent insert does not have to be removed. As the biodegradable or bioerodible polymer is degraded or dissolved, the trapped azalide antibiotic is released. Although inserts can provide long term release and hence only a single application of the insert may be necessary, they are generally difficult to insert and are uncomfortable to the patient.

A preferred form of the stabilized azalide composition for administration of azalide antibiotics to the ocular and periocular tissues is an aqueous polymeric suspension. Here, at least one of the azalide antibiotic or the polymeric suspending agent is suspended in an aqueous medium having the properties as described above. The azalide antibiotic may be in suspension, although in the preferred pH ranges the azalide antibiotic will be in solution (water soluble), or both in solution and in suspension. It is possible for significant amounts of the azalide antibiotic to be present in suspension. The polymeric suspending agent is preferably in suspension (i.e. water insoluble and/or water swellable), although water soluble suspending agents are also suitable for use with a suspension of the azalide antibiotic. The suspending agent serves to provide stability to the suspension and to increase the residence time of the dosage form on the eye. It can also enhance the sustained release of the drug in terms of both longer release times and a more uniform release curve.

Examples of polymeric suspending agents include dextrans, polyethylene glycols, polyvinylpyrolidone, polysaccharide gels, Gelrite®, cellulosic polymers like hydroxypropyl methylcellulose, and carboxy-containing polymers such as polymers or copolymers of acrylic acid, as well as other polymeric demulcents. A preferred polymeric suspending agent is a water swellable, water insoluble polymer, especially a crosslinked carboxy-containing polymer.

Crosslinked carboxy-containing polymers used in practicing this invention are, in general, well known in the art. In a preferred embodiment such polymers may be prepared from at least about 90%, and preferably from about 95% to about 99.9% by weight, based on the total weight of monomers present, of one or more carboxy-containing monoethylenically unsaturated monomers (also occasionally referred to herein as carboxy-vinyl polymers). Acrylic acid is the preferred carboxy-containing monoethylenically unsaturated monomer, but other unsaturated, polymerizable carboxy-containing monomers, such as methacrylic acid, ethacrylic acid, β-methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, β-phenylacrylic acid (cinnamic acid), coumaric acid (o-hydroxycinnamic acid), umbellic acid (p-hydroxycoumaric acid), and the like can be used in addition to or instead of acrylic acid.

Such polymers may be crosslinked by a polyfunctional crosslinking agent, preferably a difunctional crosslinking agent. The amount of crosslinking should be sufficient to form insoluble polymer particles, but not so great as to unduly interfere with sustained release of the azalide antibiotic. Typically the polymers are only lightly crosslinked. Preferably the crosslinking agent is contained in an amount of from about 0.01% to about 5%, preferably from about 0.1% to about 5.0%, and more preferably from about 0.2% to about 1%, based on the total weight of monomers present. Included among such crosslinking agents are non-polyalkenyl polyether difunctional crosslinking monomers such as divinyl glycol; 2,3-dihydroxyhexa-1,5-diene; 2,5-dimethyl-1,5-hexadiene; divinylbenzene; N,N-diallylacrylamide; N,N-diallymethacrylamide and the like. Also included are polyalkenyl polyether crosslinking agents containing two or more alkenyl ether groupings per molecule, preferably alkenyl ether groupings containing terminal $H_2C=C<$ groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; see, e.g., Brown U.S. Pat. No. 2,798,053, the entire contents of which are incorporated herein by reference. Diolefinic non-hydrophilic macromeric crosslinking agents having molecular weights of from about 400 to about 8,000, such as insoluble di- and polyacrylates and methacrylates of diols and polyols, diisocyanate-hydroxyalkyl acrylate or methacrylate reaction products of isocyanate terminated prepolymers derived from polyester diols, polyether diols or polysiloxane diols with hydroxyalkylmethacrylates, and the like, can also be used as the crosslinking agents; see, e.g., Mueller et al. U.S. Pat. Nos. 4,192,827 and 4,136,250, the entire contents of each patent being incorporated herein by reference.

The crosslinked carboxy-vinyl polymers may be made from a carboxy-vinyl monomer or monomers as the sole monoethylenically unsaturated monomer present, together with a crosslinking agent or agents. Preferably the polymers are ones in which up to about 40%, and preferably from about 0% to about 20% by weight, of the carboxy-containing monoethylenically unsaturated monomer or monomers has been replaced by one or more non-carboxyl-containing monoethylenically unsaturated monomer or monomers containing only physiologically and ophthalmically innocuous substituents, including acrylic and methacrylic acid esters such as methyl methacrylate, ethyl acrylate, butyl acrylate, 2-ethylhexylacrylate, octyl methacrylate, 2-hydroxyethylmethacrylate, 3-hydroxypropylacrylate, and the like, vinyl acetate, N-vinylpyrrolidone, and the like; see Mueller et al. U.S. Pat. No. 4,548,990 for a more extensive listing of such additional monoethylenically unsaturated monomers.

Particularly preferred polymers are lightly crosslinked acrylic acid polymers wherein the crosslinking monomer is 2,3-dihydroxyhexa-1,5-diene or 2,3-dimethylhexa-1,5-diene. Preferred commercially available polymers include polycarbophil (Noveon AA-1) and Carbopol®. Most preferably, a carboxy-containing polymer system known by the tradename DuraSite®, containing polycarbophil, which is a sustained release topical ophthalmic delivery system that releases the drug at a controlled rate, is used in the aqueous polymeric suspension composition of the present invention.

The crosslinked carboxy-vinyl polymers used in practicing this invention are preferably prepared by suspension or emulsion polymerizing the monomers, using conventional free radical polymerization catalysts, to a dry particle size of not more than about 50 μm in equivalent spherical diameter; e.g., to provide dry polymer particles ranging in size from about 1 to about 30 μm, and preferably from about 3 to about 20 μm, in equivalent spherical diameter. Using polymer particles that were obtained by mechanically milling larger polymer particles to this size is preferably avoided. In general, such polymers will have a molecular weight which has been variously reported as being from about 250,000 to about 4,000,000, and from 3,000,000,000 to 4,000,000,000.

In a more preferred embodiment of the invention for topical ophthalmic administration, the particles of crosslinked carboxy-vinyl polymer are monodisperse, meaning that they have a particle size distribution such that at least 80% of the particles fall within a 10 μm band of major particle size distribution. More preferably, at least 90% and most preferably at least 95%, of the particles fall within a 10 μm band of major particle size distribution. Also, a monodisperse particle size means that there is no more than 20%, preferably no more than 10%, and most preferably no more than 5% particles of a size below 1 μm. The use of a monodispersion of particles will give maximum viscosity and an increased eye residence time of the ophthalmic medicament delivery system for a given particle size. Monodisperse particles having a particle size of 30 μm and below are most preferred. Good particle packing is aided by a narrow particle size distribution.

The aqueous polymeric suspension normally contains azalide antibiotics in an amount from about 0.05% to about 25%, preferably about 0.1% to about 20%, more preferably about 0.5% to about 15%, more preferably about 1% to about 12%, more preferably about 2% to about 10.0%, and polymeric suspending agent in an amount from about 0.05% to about 10%, preferably about 0.1% to about 5% and more preferably from about 0.2% to about 1.0% polymeric suspending agent. In the case of the above described water insoluble, water-swellable crosslinked carboxy-vinyl polymer, another preferred amount of the polymeric suspending agent is an amount from about 0.5% to about 2.0%, preferably from about 0.5% to about 1.2%, and in certain embodiments from about 0.6% to about 0.9%, based on the weight of the composition. Although referred to in the singular, it should be understood that one or 25 more species of polymeric suspending agent, such as the crosslinked carboxy-containing polymer, can be used with the total amount falling within the stated ranges. In one preferred embodiment, the composition contains about 0.6% to about 0.8% of a polycarbophil such as NOVEON AA-1.

In one embodiment, the amount of insoluble lightly crosslinked carboxy-vinyl polymer particles, the pH, and the osmotic pressure can be correlated with each other and with the degree of crosslinking to give a composition having a viscosity in the range of from about 500 to about 100,000 centipoise, and preferably from about 1,000 to about 30,000 or about 1,000 to about 10,000 centipoise, as measured at room temperature (about 25° C.) using a Brookfield Digital LVT Viscometer equipped with a number 25 spindle and a 13R small sample adapter at 12 rpm (Brookfield Engineering Laboratories Inc.; Middleboro, Mass.). Alternatively, when the viscosity is within the range of 500 to 3000 centipoise, it may be determined by a Brookfield Model DV-11+, choosing a number cp-52 spindle at 6 rpm.

When water soluble polymers are used as the suspending agent, such as hydroxypropyl methylcellulose, the viscosity will typically be about 10 to about 400 centipoise, more typically about 10 to about 200 centipoises or about 10 to about 25 centipoise.

The stabilized azalide antibiotic formulations of the instant invention containing aqueous polymeric suspensions may be formulated so that they retain the same or substantially the same viscosity in the eye that they had prior to administration to the eye. Alternatively, in the most preferred embodiments for ocular administration, they may be formulated so that there is increased gelation upon contact with tear fluid. For instance, when a stabilized formulation containing DuraSite® or other similar polyacrylic acid-type polymer at a pH of about 5.8 to about 6.8, or more preferably about 6.0 to about 6.5, or more preferably at a pH of about 6.2 to about 6.4, or more preferably about 6.25 to about 6.35, or more preferably about 6.3 is administered to the eye, the polymer will swell upon contact with tear fluid which has a higher pH. This gelation or increase in gelation leads to entrapment of the suspended azalide antibiotic particles, thereby extending the residence time of the composition in the eye. The azalide antibiotic is released slowly as the suspended particles dissolve over time. All these events eventually lead to increased patient comfort and increased azalide antibiotic contact time with the eye tissues, thereby increasing the extent of drug absorption and duration of action of the formulation in the eye. These compositions advantageously combine stability and solubility characteristics of azalide antibiotics, which display minimal degradation and relatively high solubility in aqueous compositions at the pre-administration pH, with the advantages of the gelling composition.

The viscous gels that result from fluid eye drops typically have residence times in the eye ranging from about 2 to about 12 hours, e.g., from about 3 to about 6 hours. The agents contained in these drug delivery systems will be released from the gels at rates that depend on such factors as the drug itself and its physical form, the extent of drug loading and the pH of the system, as well as on any drug delivery adjuvants, such as ion exchange resins compatible with the ocular surface, which may also be present.

The stabilized azalide compositions of the present invention can be prepared from known or readily available materials through the application of known techniques. The azalide antibiotics used in the present invention are commercially available or readily obtained through known reaction techniques. In particular, the azalide antibiotics can be formed from erythromycin A, a naturally occurring compound formed during the culturing of a strain of *Streptomyces erythreus*. However, it is not required that the azalide antibiotic actually be formed from erythromycin. In addition, the azalide antibiotic can be combined with the other ingredients in the chosen dosage form by conventional methods known in the art.

As discussed above the stabilized azalide antibiotic-containing composition of the instant invention can be formulated for administration via a variety of routes. The compositions can be administered to humans and a variety of non-human animals, the latter including but not limited to cows, sheep, horses, pigs, goats, rabbits, dogs, cats, and other mammals. Suitably formulated compositions can be administered parenterally, orally, or topically. In a preferred embodiment, suitable formulations are topically applied to the eye for the treatment of an infection in the eye or as a preventive such as prior to surgery.

In addition to those components recited above, the compositions of this invention may contain one or more of the following: surfactants, adjuvants including additional medicaments, buffers, antioxidants, tonicity adjusters, preservatives, thickeners or viscosity modifiers, and the like. Additives in the formulation may desirably include sodium chloride, EDTA (disodium edetate), and/or BAK (benzalkonium chloride), sorbic acid, methyl paraben, propyl paraben, and chlorhexidine. Other excipients compatible with various routes of adminsitration such as topical and parenteral administration are outlined in *Remington's Pharmaceutical Sciences*, Mack Publishing Co., Easton, Pa., 18$^{th}$ edition (1990).

A further aspect of the present invention involves the above-mentioned use of additional medicaments in combination with the azalide antibiotic. A composition comprising an azalide antibiotic, an additional medicament, and an ophthalmically acceptable carrier can advantageously simplify administration and allow for treating or preventing multiple conditions or symptoms simultaneously. The "additional medicaments," which can be present in any of the ophthalmic compositional forms described herein including fluid and solid forms, are pharmaceutically active compounds having efficacy in ocular application and which are compatible with an azalide antibiotic and with the eye. Typically, the additional medicaments include other antibiotics, antivirals, antifungals, anesthetics, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; sulfonamides; polymyxin; chloramphenicol; neomycin; paramomomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; comolyn; lodoxamide; levocabastin; naphazoling; antazoline; and pheniramimane. These other medicaments are generally present in a therapeutically effective amount. These amounts are generally within the range of from about 0.01 to 5%, more typically 0.1 to 2%, for fluid compositions and typically from 0.5 to 50% for solid dosage forms.

The aqueous compositions (solutions or suspensions) for use in the present invention preferably use water that has no physiologically or ophthalmically harmful constituents. Typically purified or deionized water is used. The pH is adjusted by adding any physiologically and ophthalmically acceptable pH adjusting acids, bases, or buffers to within the range of about 5.0 to about 7.0, more preferably from about 5.8 to about 6.8, more preferably about 6.0 to about 6.5, more preferably at a pH of about 6.2 to about 6.4, more preferably about 6.25 to about 6.35, or more preferably about 6.3. In alternative embodiments, the azalide compositions of the present invention can be adjusted to a pH in the range of 5.0 to about 6.0, or more preferably about 5.5 to about 5.95, or more preferably 5.6 to 5.9. Any of the aforementioned ranges can be used with any of the compositions of the present invention, including, without limitation, intravenous and topical embodiments. Examples of acids include acetic, boric, citric, lactic, phosphoric, hydrochloric, and the like, and examples of bases include potassium hydroxide, sodium hydroxide, sodium phosphate, sodium borate, sodium citrate, sodium acetate, sodium lactate, tromethamine, THAM (trishydroxymethylaminomethane), and the like. Salts and buffers include but are not limited to citrate/dextrose, sodium bicarbonate, ammonium chloride and mixtures of the aforementioned acids and bases. The pH is preferably adjusted by adding sodium hydroxide.

All of the percentages recited herein refer to weight percent, unless otherwise indicated. The following non-limiting examples serve to illustrate certain features of the present invention. The compositions and amounts used for Examples 1–7 are summarized in Table 1, for Examples 9–14 in Table 2, for Example 17 in Table 3, for Example 20 in Tables 4–11, and for Example 21 in Table 12.

EXAMPLES 1–2

Hydroxypropylmethyl cellulose, sodium chloride, edetate sodium (EDTA), BAK and surfactant are dissolved in a beaker containing approximately ⅓ of the final weight of water and stirred for 10 minutes with an overhead stirring. The azithromycin is added and stirred to disperse for 30 minutes. The solution is sterilized by autoclaving at 121° C. for 20 minutes. Alternately, the azithromycin may be dry heat sterilized and added by aseptic powder addition after sterilization. Mannitol, Poloxamer 407, and boric acid are dissolved separately in approximately ½ of the final weight of water and added by sterile filtration (0.22 μm filter) and stirred for 10 minutes to form a mixture. The mixture is adjusted to the desired pH in the range of 5.8 to 7.0 with sterile sodium hydroxide (1N to 10N) while stirring, brought to a final weight with sterile water, and aseptically transferred to multi-dose containers.

EXAMPLES 3–6

Noveon AA-1 is slowly dispensed into a beaker containing approximately ⅓ of the final weight of water and stirred for 1.5 hrs. with an overhead stirrer. Noveon AA-1 is an acrylic acid polymer available from B. F. Goodrich. Edetate sodium (EDTA), BAK, sodium chloride, and surfactant are then added to the polymer solution and stirred for 10 minutes after each addition. The polymer suspension is at a pH of about 3.0–3.5. The azithromycin is added and stirred to disperse for 30 minutes. The pH of the mixture is titrated to the desired pH in the range of 5.8 to 6.8, and brought to final weight/volume with water. The mixture is aliquoted into single or multiple dose containers, which are sterilized by autoclaving at 121° C., for 20 minutes. Alternately, the azithromycin may be dry heat sterilized and added by aseptic powder addition after sterilization. In the alternative embodiment Noveon AA-1 is slowly dispensed into a beaker containing approximately ⅓ of the final weight of water and stirred for 1.5 hrs. with overhead stirring to form a Noveon suspension. The Noveon suspension is sterilized by autoclaving at 121° C., for 20 minutes. Solutions containing mannitol and boric acid, or solutions containing Dequest, mannitol, and boric acid are dissolved separately in approximately ½ of the final weight of water, added to the sterilized Noveon polymer suspension by sterile filtration (0.22 μm filter), and stirred for 10 minutes. The dry heat sterilized azithromycin is then added by aseptic powder addition. The mixture is adjusted to the desired pH with sterile sodium hydroxide (1N to 10N) while stirring, brought to final weight with sterile water, and aseptically filled into multi-dose containers.

EXAMPLE 7

Noveon AA-1 is slowly dispensed into a beaker containing approximately ½ of the final weight of water and stirred for 1.5 hrs. with overhead stirring. Noveon AA-1 is an acrylic acid polymer available from B. F. Goodrich. Edetate sodium (EDTA), Poloxamer 407, and sodium chloride are then added to the polymer suspension and stirred for 10 minutes. The polymer suspension is at a pH of about 3.0–3.5. The azithromycin is added and stirred to disperse for 30 minutes. The mixture is adjusted to desired pH with sodium hydroxide (1N to 10N) while stirring, and is sterilized by autoclaving at 121° C. for 20 minutes. Alternately, the azithromycin may be dry heat sterilized and added by aseptic powder addition after sterilization. Mannitol is dissolved in ⅒ of the final weight of water and sterile filtered (0.22 μm filter) in to the polymer suspension and stirred for 10 minutes. The mixture is adjusted to desired pH with sterile sodium hydroxide (1N to 10N) while stirring, brought to final weight with sterile water, and aseptically filled into unit-dose containers.

TABLE 1

Formulation Examples 1–7

| Ingredient | 1% | 2% | 3% | 4% | 5% | 6% | 7% |
|---|---|---|---|---|---|---|---|
| Azithromycin | 0.10 | 0.50 | 0.10 | 0.50 | 0.50 | 0.50 | 0.10 |
| Hydroxypropylmethyl Cellulose | 1.50 | 2.00 | — | — | — | — | — |
| Noveon AA-1 | — | — | 0.80 | 0.80 | 0.80 | 0.80 | 0.80 |
| Sodium Chloride | 0.20 | 0.20 | 0.20 | 0.20 | 0.20 | 0.20 | 0.30 |
| Mannitol | 1.50 | 1.50 | 1.50 | 1.50 | 1.50 | 1.50 | 1.50 |
| Edetate Disodium | 0.10 | 0.10 | 0.10 | 0.10 | 0.10 | 0.10 | 0.10 |
| Poloxamer 407 | 0.10 | 0.10 | 0.10 | 0.10 | 0.10 | 0.10 | 0.10 |
| Benzalkonium Chloride | 0.01 | 0.01 | 0.01 | 0.01 | — | 0.01 | — |
| Dequest 2060S | — | — | — | — | 0.10 | — | — |
| Boric Acid | 0.50 | 0.50 | 0.50 | 0.50 | 0.50 | 0.50 | — |
| Sodium Hydroxide | q.s. to pH 7 | q.s. to pH 7 | q.s. to pH 6 | q.s. to pH 6 | q.s. to pH 6 | q.s. to pH 6 | q.s. to pH 6 |
| Water | q.s. to 100 | q.s. to 100 | q.s. to 100 | q.s. to 100 | q.s. to 100 | q.s. to 100 | q.s. to 100 |

EXAMPLE 8

An azithromycin ointment is prepared by dissolving 0.3 grams of azithromycin and 0.5 grams of chlorobutanol in a mixture containing 3.0 grams mineral oil/96.2 grams white petrolatum by stirring in a 100 ml beaker while heating sufficiently to dissolve both compounds. The mixture is sterile filtered through a 0.22 μm filter at a sufficient temperature to be filtered and filled aseptically into sterile ophthalmic ointment tubes.

EXAMPLE 9–11

Hydroxypropylmethyl cellulose (HPMC), sodium chloride, edetate sodium (EDTA), and surfactant are dissolved in a beaker containing approximately ⅓ of the final weight of water and stirred for 10 minutes with an overhead stirrer. The mixture is sterilized by autoclaving at 121° C., for 20 minutes. The azithromycin and steroid, as indicated in table 2, are dry heat sterilized and added to the HPMC-containing solution by aseptic powder addition. Mannitol, Poloxamer 407, BAK, and boric acid are dissolved separately in approximately ½ of the final weight of water and added by sterile filtration (0.22 um filter) and stirred for 10 minutes to form a mixture. The mixture is adjusted to the desired pH with sterile sodium hydroxide (1N to 10N) while stirring, brought to a final weight with sterile water, and aseptically dispensed into multi-dose containers.

EXAMPLES 12–14

Noveon AA-1 is slowly dispersed into a beaker containing approximately ⅓ of the final weight of water and stirred for 1.5 hrs. with an overhead stirrer. Noveon AA-1 is an acrylic acid polymer available from B. F. Goodrich. Edetate sodium (EDTA), sodium chloride, and surfactant are then added to the polymer solution and stirred for 10 minutes after each addition. The polymer suspension is at a pH of about 3.0–3.5. The mixture is sterilized by autoclaving at 121° C. for 20 minutes. The azithromycin and steroid, as indicated in table 2, are dry heat sterilized and added to the polymer suspension by aseptic powder addition. BAK, mannitol, and boric acid are dissolved separately in approximately ½ of the final weight of water, added to the polymer mixture by sterile filtration (0.22 um filter) and stirred for 10 minutes. The mixture is adjusted to the desired pH with sterile sodium hydroxide (1N to 10N) while stirring, brought to a final weight with sterile water, and aseptically dispensed into multi-dose containers.

TABLE 2

| | Formulation Examples 9–14 | | | | | |
|---|---|---|---|---|---|---|
| Ingredient | 9% | 10% | 11% | 12% | 13% | 14% |
| Azithromycin | 0.10 | 0.10 | 0.10 | 0.10 | 0.10 | 0.10 |
| Prednisolone Acetate | 0.10 | — | — | 0.10 | — | — |
| Fluorometholone | — | 0.10 | — | — | 0.10 | — |
| Dexamethasone | — | — | 0.10 | — | — | 0.10 |
| Hydroxypropylmethyl Cellulose | 1.50 | 1.50 | 1.50 | — | — | — |
| Noveon AA-1 | — | — | — | 0.80 | 0.80 | 0.80 |
| Sodium Chloride | 0.20 | 0.20 | 0.20 | 0.20 | 0.20 | 0.20 |
| Mannitol | 1.50 | 1.50 | 1.50 | 1.50 | 1.50 | 1.50 |
| Edetate Disodium | 0.10 | 0.10 | 0.10 | 0.10 | 0.10 | 0.10 |
| Poloxamer 407 | 0.10 | 0.10 | 0.10 | 0.10 | 0.10 | 0.10 |
| Benzalkonium Chloride | 0.01 | 0.01 | 0.01 | 0.01 | 0.01 | 0.01 |
| Boric Acid | 0.50 | 0.50 | 0.50 | 0.50 | 0.50 | 0.50 |
| Sodium Hydroxide | q.s. to pH 7 | q.s. to pH 7 | q.s. to pH 7 | q.s. to pH 6 | q.s. to pH 6 | q.s. to pH 6 |
| Water | q.s. to 100 | q.s. to 100 | q.s. to 100 | q.s. to 100 | q.s. to 100 | q.s. to 100 |

EXAMPLE 15 pH Solubility Profiles

The solubility of azithromycin is measured as a function of pH in 0.2 M citric acid buffer over the range of pH 5.91 to 9.0. FIG. 1 shows the results of the solubility measurements and the decrease in solubility as the pH of the solution is raised.

EXAMPLE 16 pH-Stability Thermal Profiles

Figure 2:
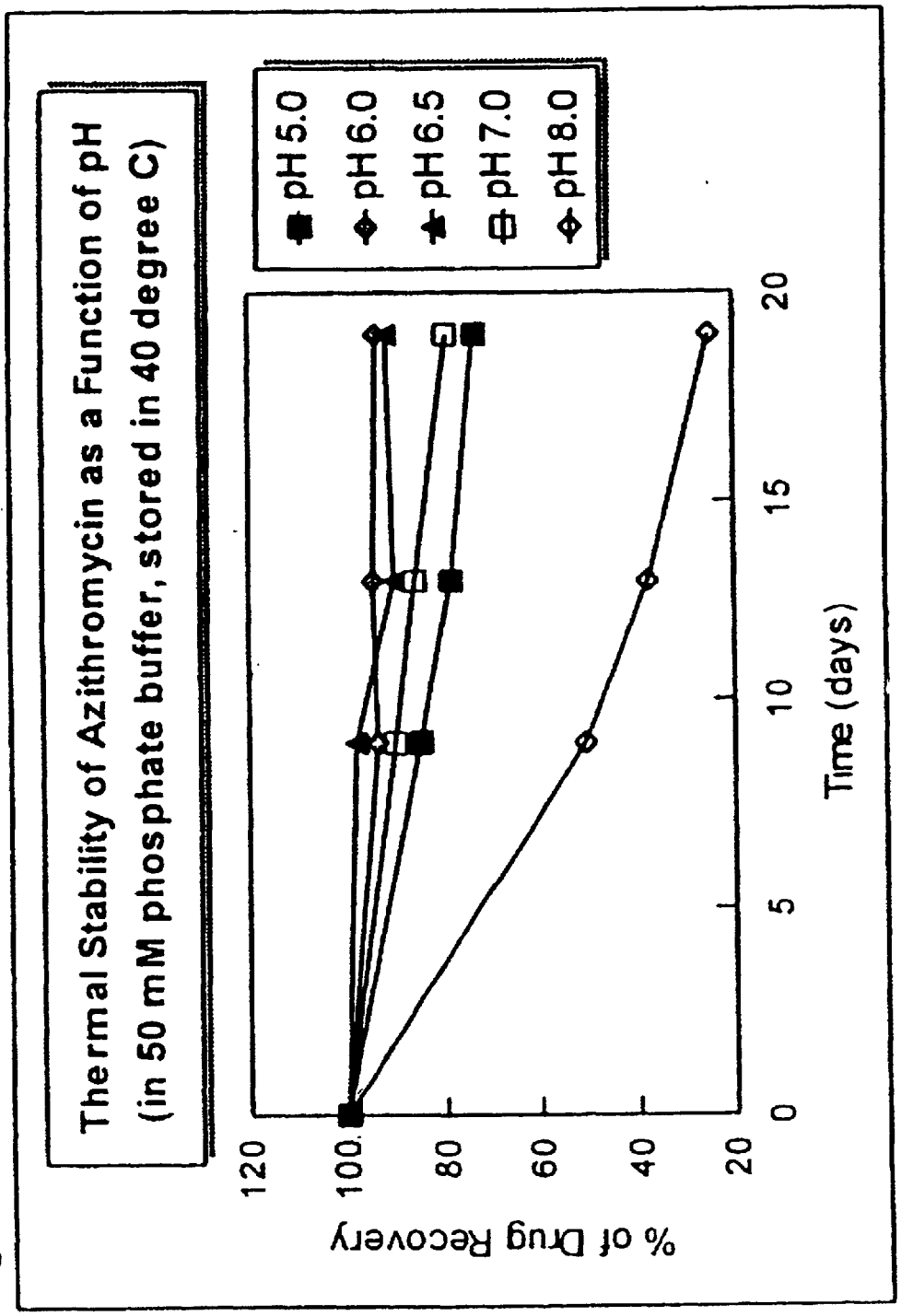
FIG. 2 is a graph depicting thermal stability of azithromycin as a function of pH at 40° C.
Figure 3:
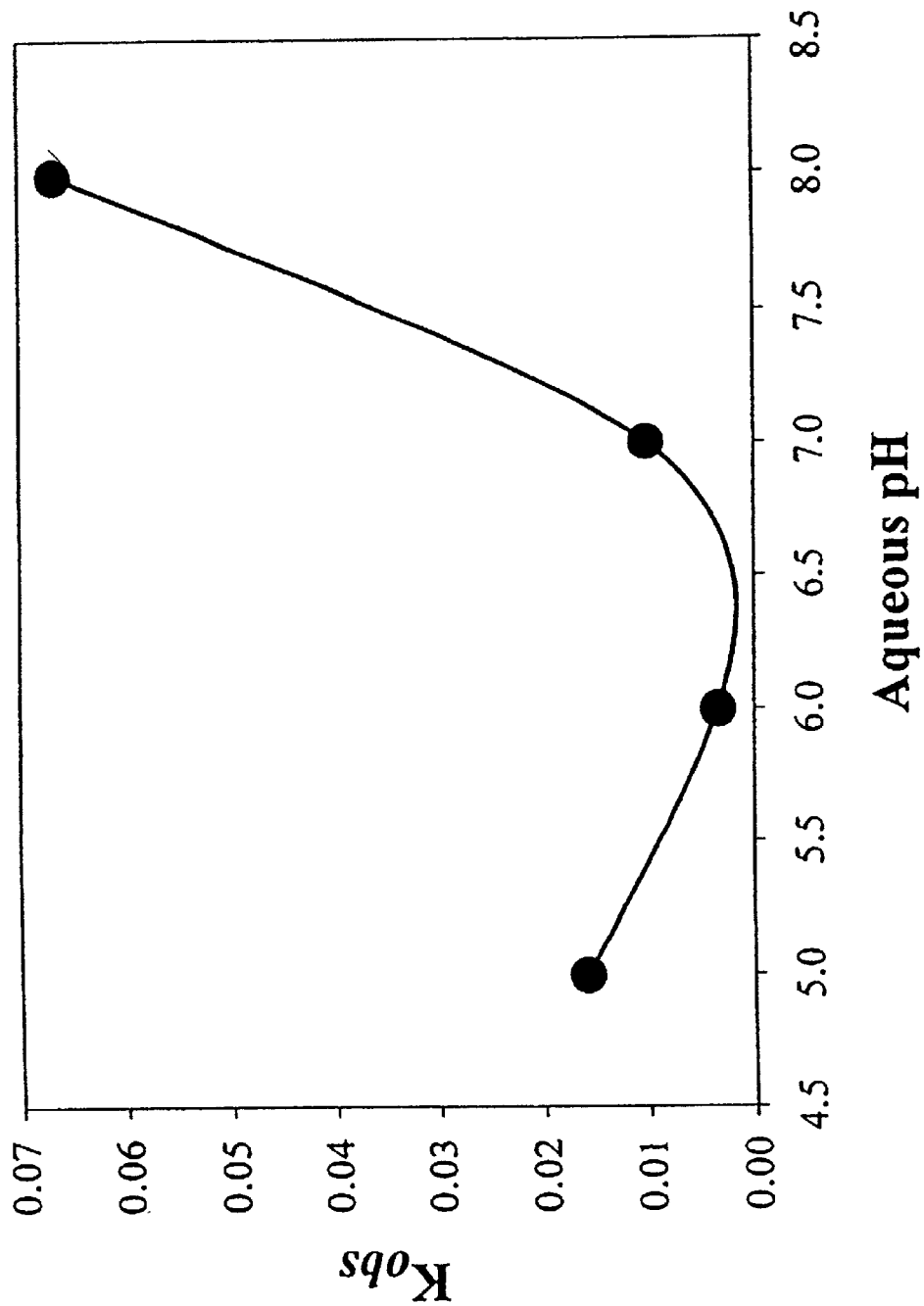
FIG. 3 is an Azithromycin pH stability profile in aqueous solution showing the dependence of the rate constant for azithromycin breakdown as a function of pH.

The thermal stability of azithromycin at 40° C. is measured in 50 mM phosphate buffer adjusted to the pH values indicated in FIG. 2. FIG. 3 is a secondary plot of data derived from the azithromycin stability profiles in FIG. 2. Azithromycin demonstrates an increased stability in the pH range from 6 to 7 with a stability optimum in the range of pH. 6–6.5. A formulation pH of 6.3 is preferred to minimize degradation of azithromycin in aqueous formulations including those that employ DuraSite®.

EXAMPLE 17

Arrhenius Plot Predictions

Figure 4:
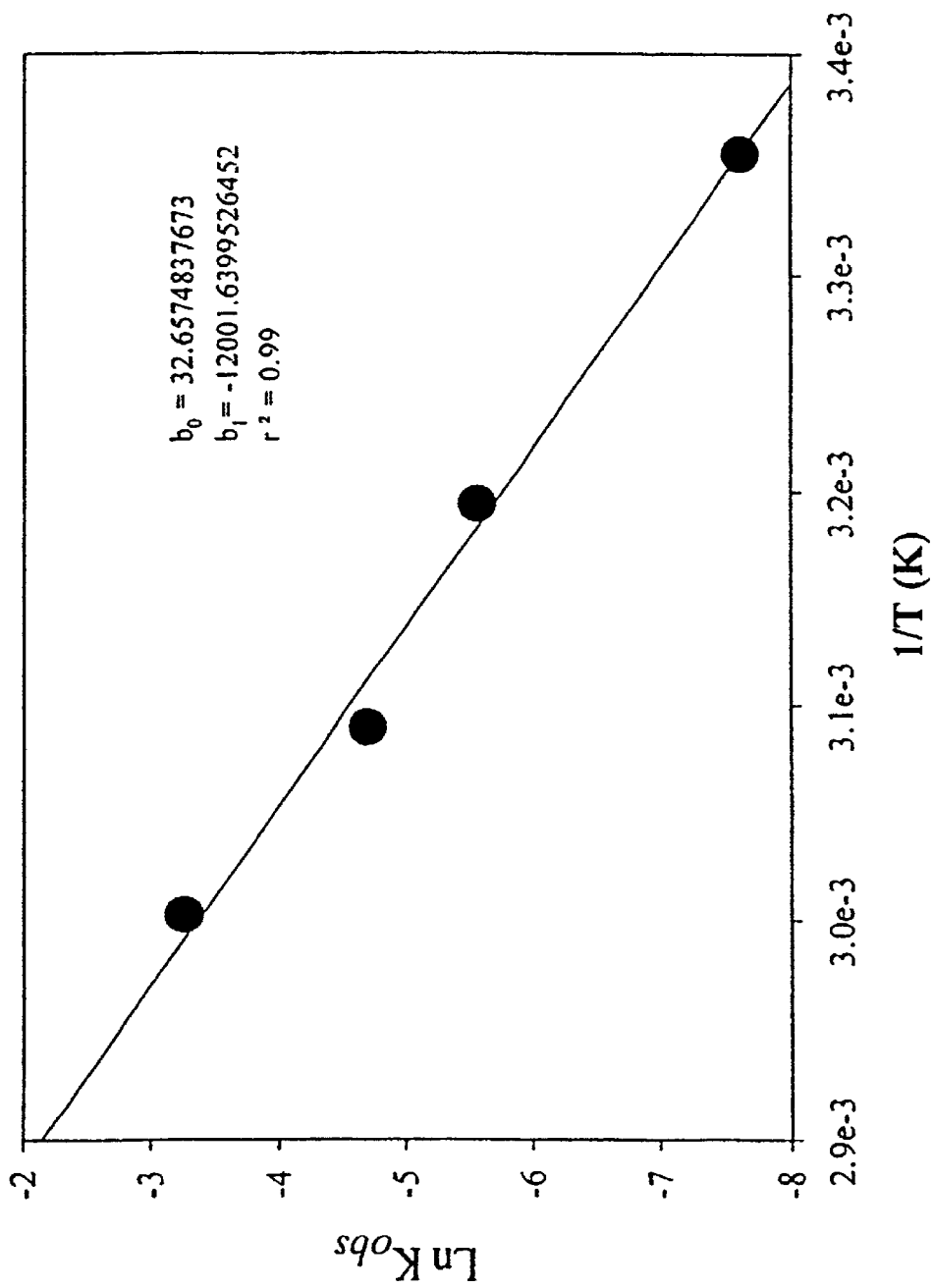
FIG. 4 is an Arrhenius Plot for ISV-401 in DuraSite Formulation at pH 6.3.

The stability of azithromycin in DuraSite® formulations is examined at 60, 50, 40 and 25° C. FIG. 4 shows an Arrhenius plot (ln $k_{obs}$ versus 1/T (K°)) for ISV-401 in DuraSite formulation. ISV 401 Dura site formulations containing azithromycin in the indicated amounts (0.5% or 1.0% w/w), are prepared in a vehicle containing the following components given on a weight to weight (w/w) basis: 0.9% polycarbophile USP, 1.0% mannitol USP, 0.4% sodium chloride USP, disodium EDTA U.S. Pat. No. 0.1%, benzalkonium chloride NF, 0.01, anhydrous citric acid NF 0.2%, sodium citrate NF 0.14% poloxamer-407 NF 0.2%, and sodium hydroxide to pH 6.3. Based on the data derived from the plot, Arrhenius equation parameters can be obtained. Using the derived equation (ln $k_{obs}$=−(12002/t+ 32.66), the shelf-life, $t_{98\%}$, is predicted to be about 24 months at 5° C. In contrast, 1.4 months shelf-life ($t_{98\%}$) is predicted at 25° C.

Table 3 (below) shows the data employed in generating the Arrhenius plot presented in FIG. 4 and the predicted results for $t_{90\%}$ and $t_{98\%}$ based on the Arrhenius equation derived from that data.

TABLE 3

Azithromycin DuraSite Formulation; Arrhenius Equation:
$LnK_{obs} = -(12002/t) + 32.66$

| Temp., ° C. | Temp., ° K. | $k_{obs}$, (day$^{-1}$) (experimental) | $k_{obs}$, (day$^{-1}$) (calculated) | $t_{90\%}$, day (or month) | $t_{98\%}$, day (or month) |
|---|---|---|---|---|---|
| 60 | 333 | 3.9 × 10$^{-2}$ | 3.4 × 10$^{-2}$ | 3 (0.1) | — |
| 50 | 323 | 9.13 × 10$^{-3}$ | 1.11 × 10$^{-2}$ | 10 (0.3) | — |
| 40 | 313 | 3.88 × 10$^{-3}$ | 3.40 × 10$^{-3}$ | 31 (1) | — |
| 25 | 298 | 4.88 × 10$^{-4}$ | 4.93 × 10$^{-4}$ | 214 (7) | 41 (1.4) |
| 5 | 278 | — | 2.72 × 10$^{-5}$ | 3873 (127) | 743 (24) |

EXAMPLE 18

Stability of Azithromycin/DuraSite Formulations

Figure 5:
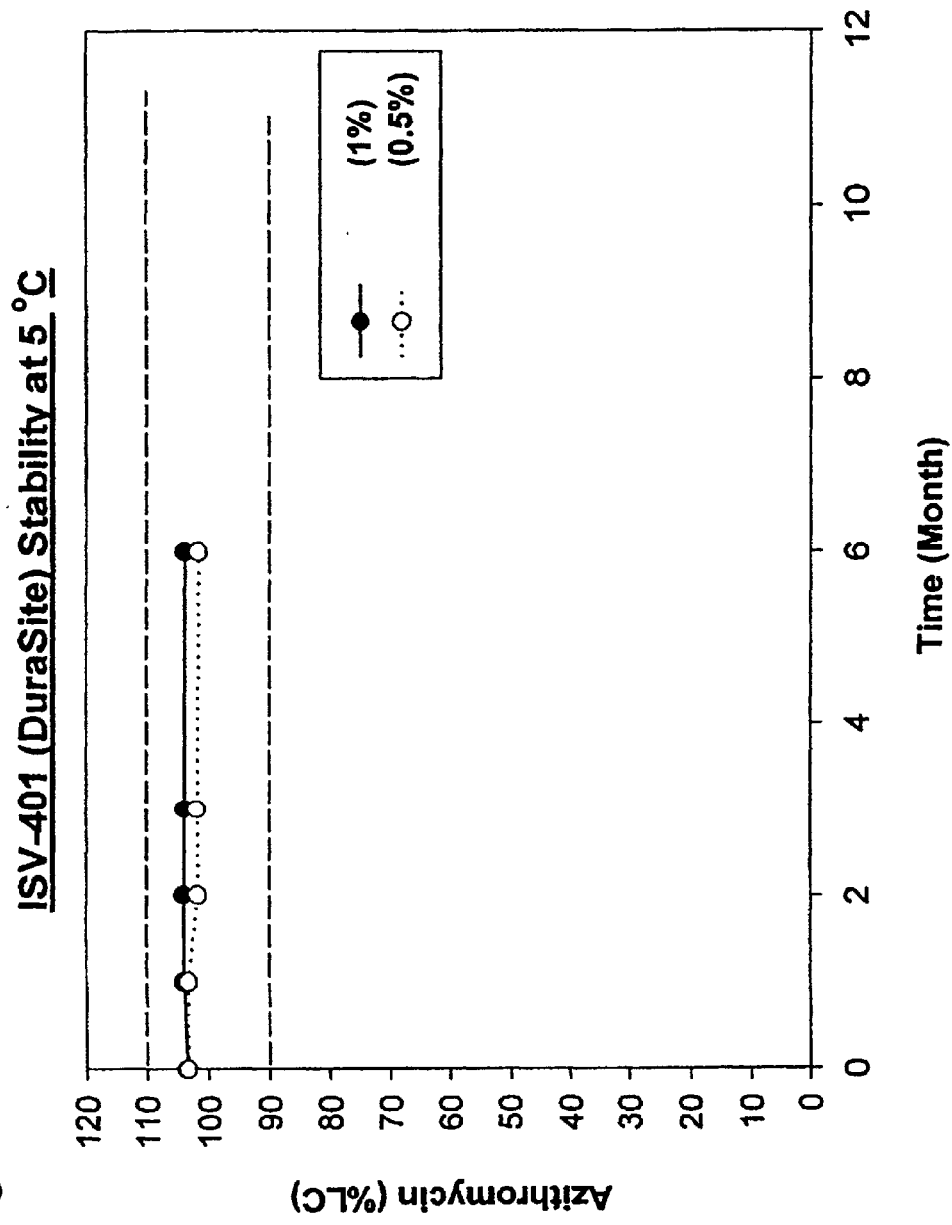
FIG. 5 is a graph showing ISV-401 (DuraSite) stability at 5° C.
Figure 6:
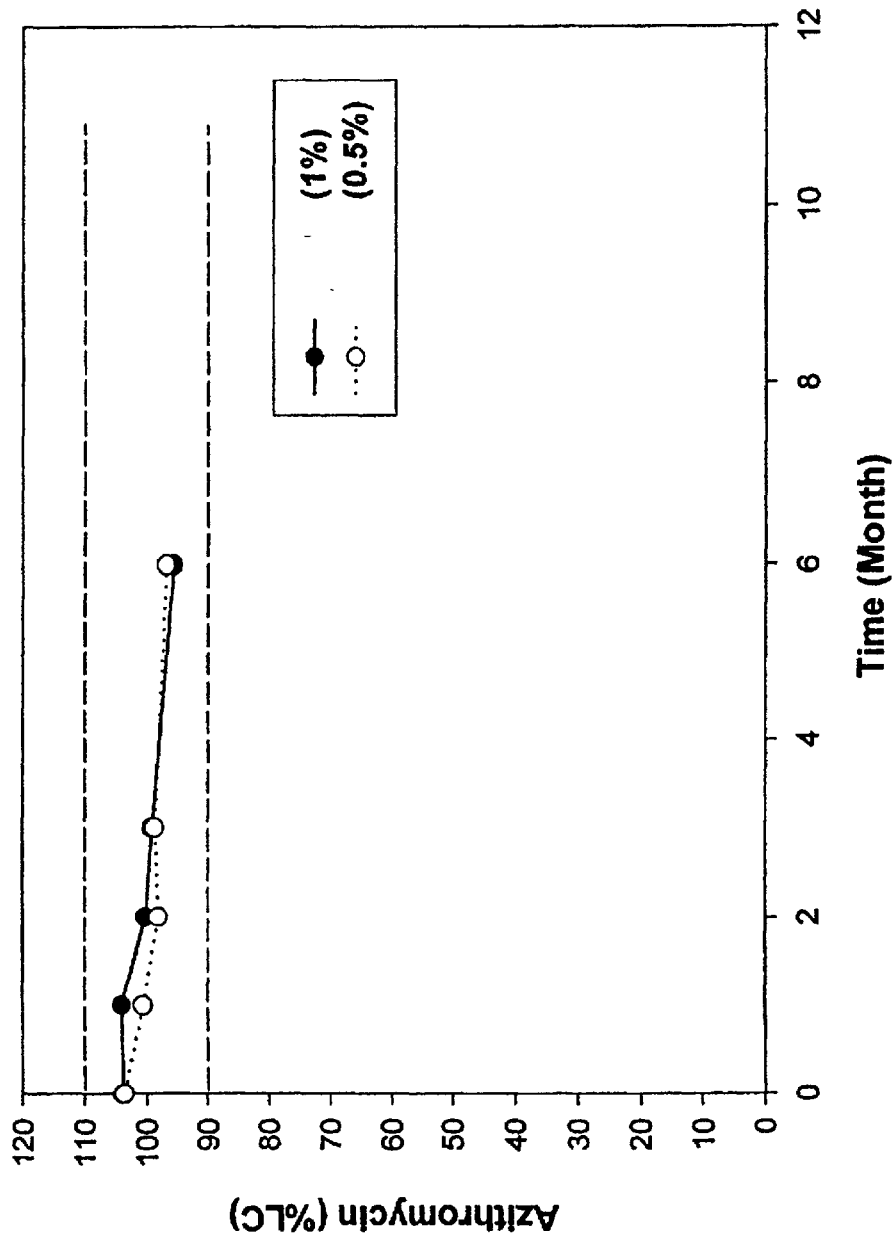
FIG. 6 is a graph showing ISV-401 (DuraSite) stability at 25° C.

The stability of ISV-401 is examined at 5° C. and 25° C. at concentrations of 0.5% and 1.0%. The product is stable at 5° C. for both concentrations of 0.5% and 1.0%. At both concentrations, approximately 7.0% azithromycin loss is observed at 25° C. after 6 months storage consistent with Arrhenius plot prediction. FIGS. 5 and 6 set forth the stability data for ISV-401 (DuraSite) at 5° C. and 25° C. respectively.

EXAMPLE 19

ISV-401 Formulation Release and Stability Specifications

Figure 7:
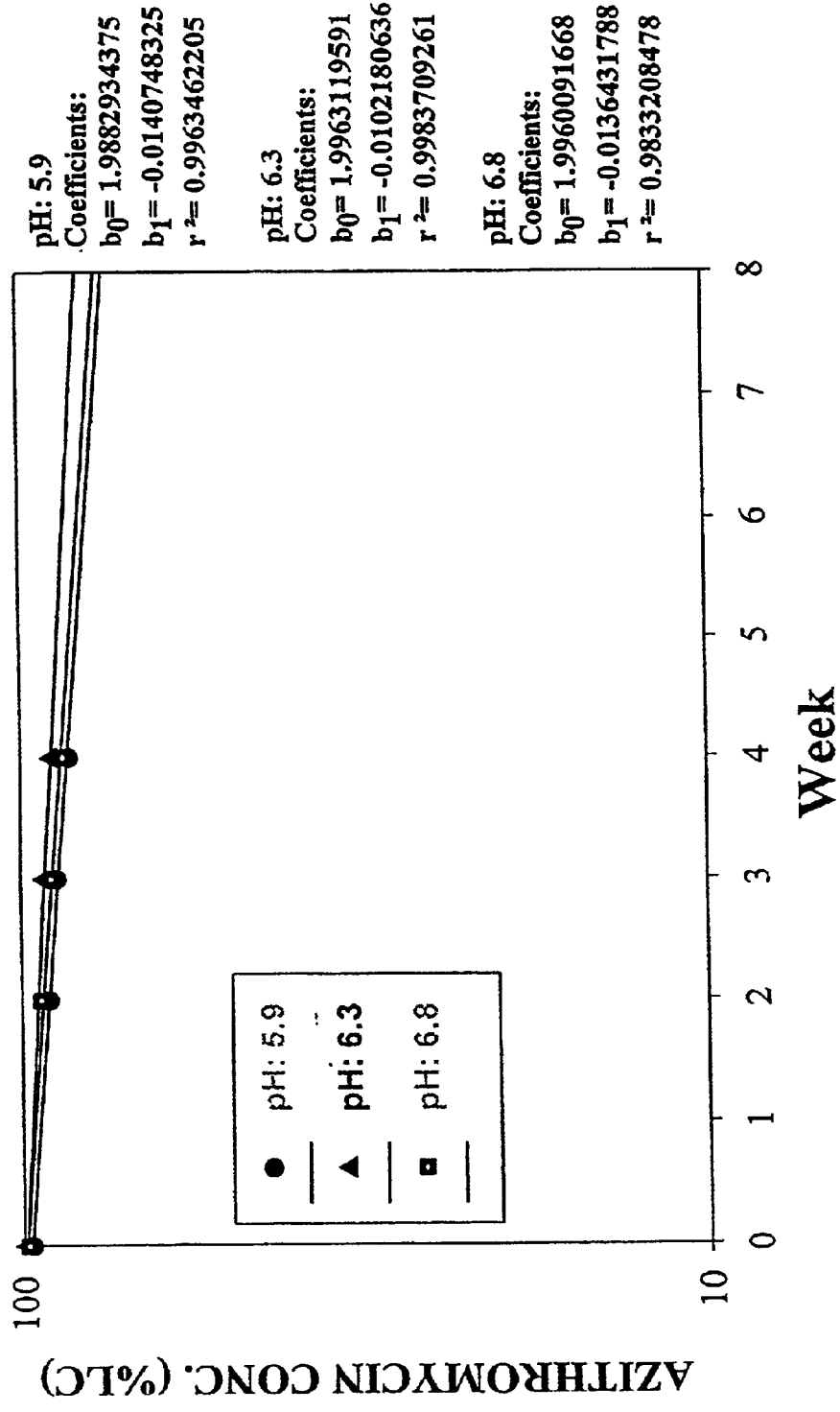
FIG. 7 is a graph depicting the pH Stability of ISV-401 at 40° C.
Figure 8:
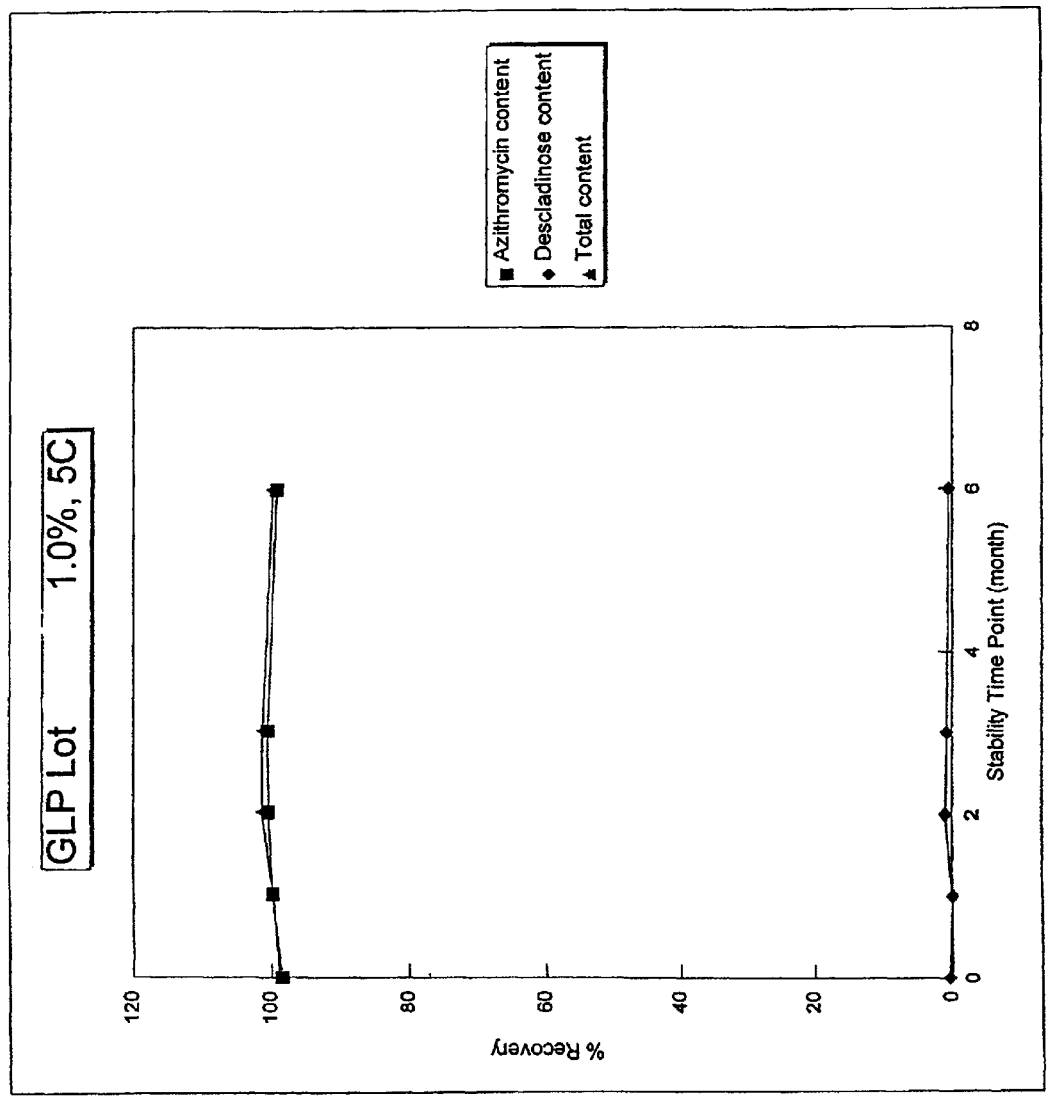
FIG. 8 is a stability graph showing the stability of a GLP Lot 1.0%, at 5° C.
Figure 9:
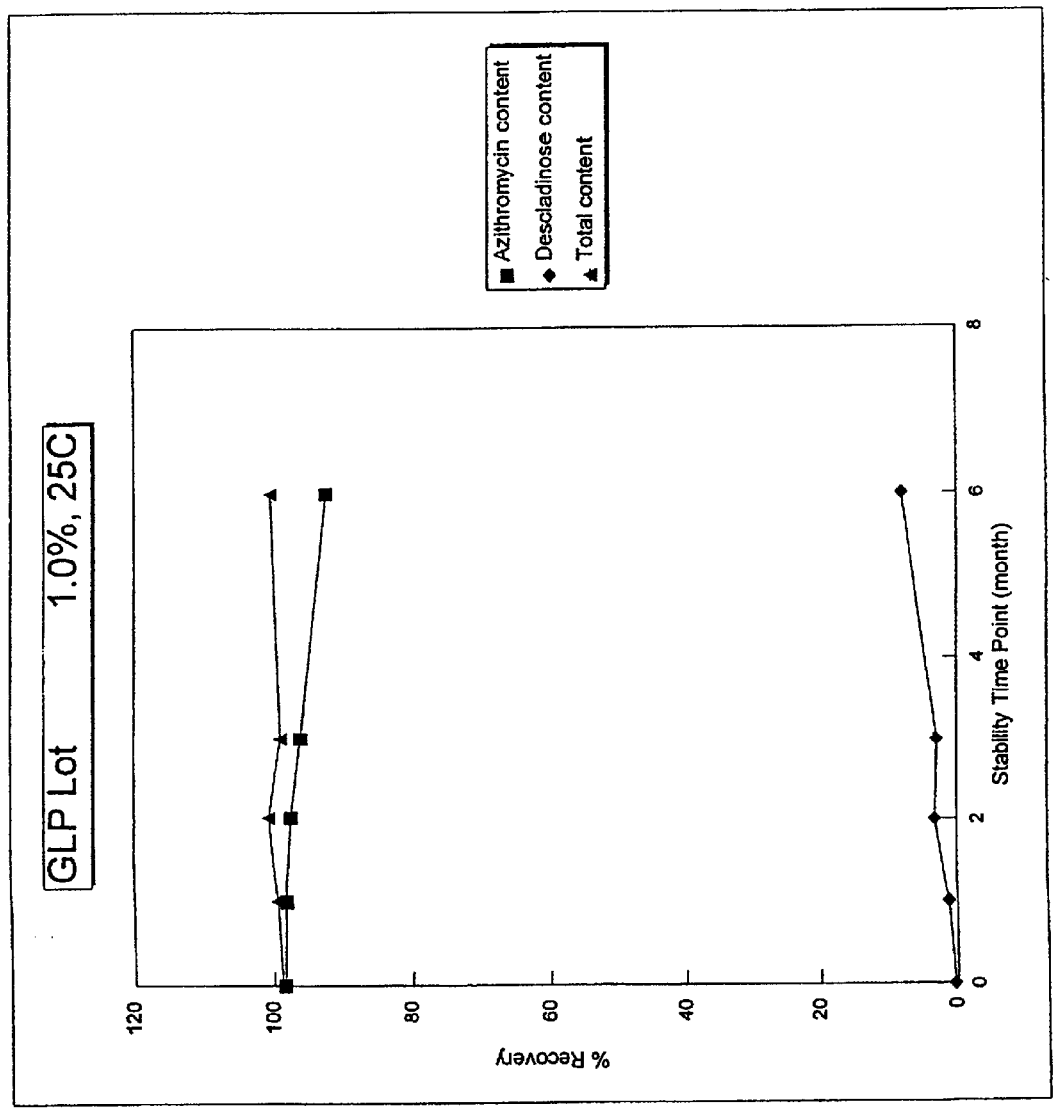
FIG. 9 is a stability graph showing the stability of a GLP Lot 1.0%, at 25° C.
Figure 10:
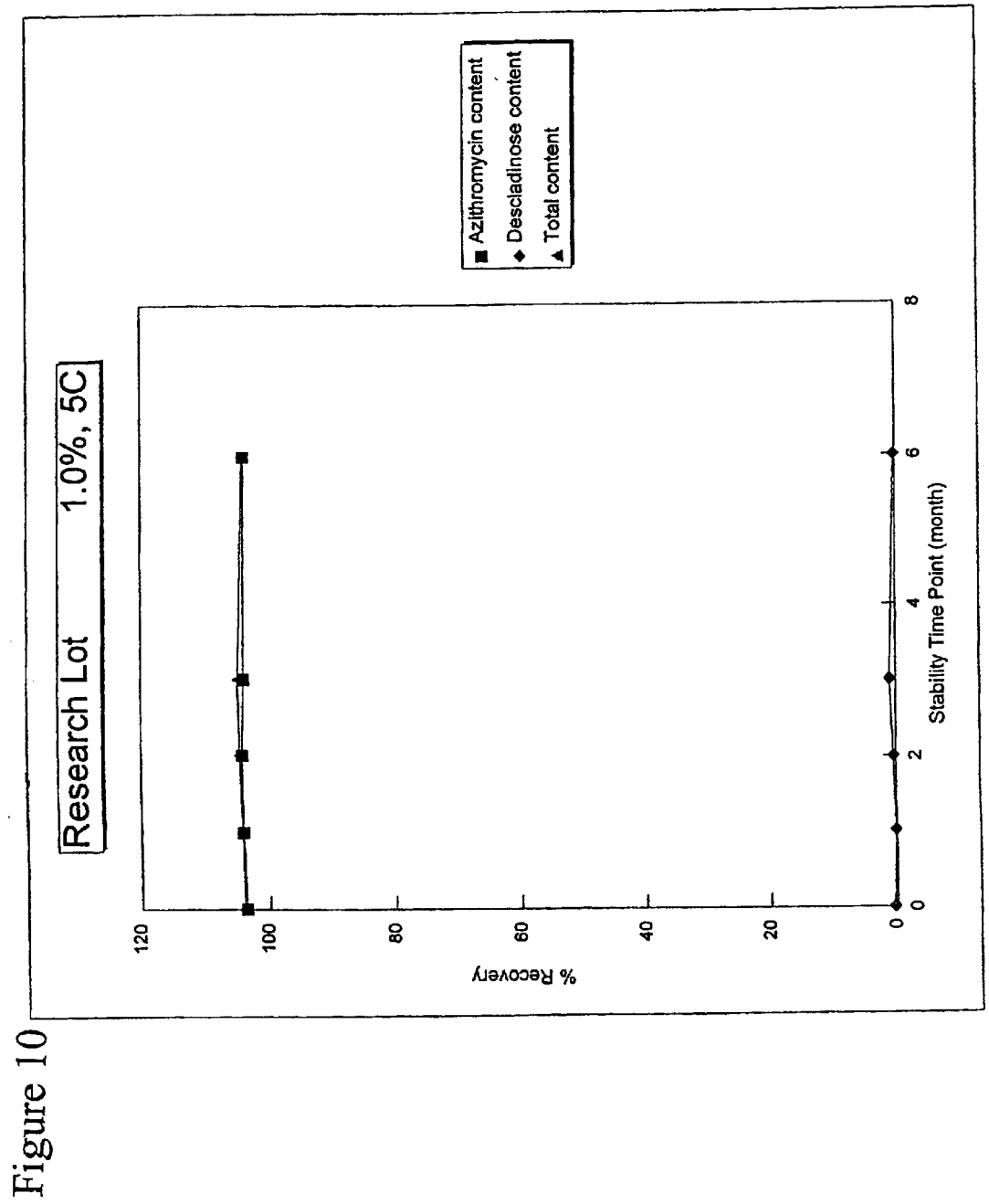
FIG. 10 is a stability graph showing the stability of a Research Lot 1.0%, at 5° C.
Figure 11:
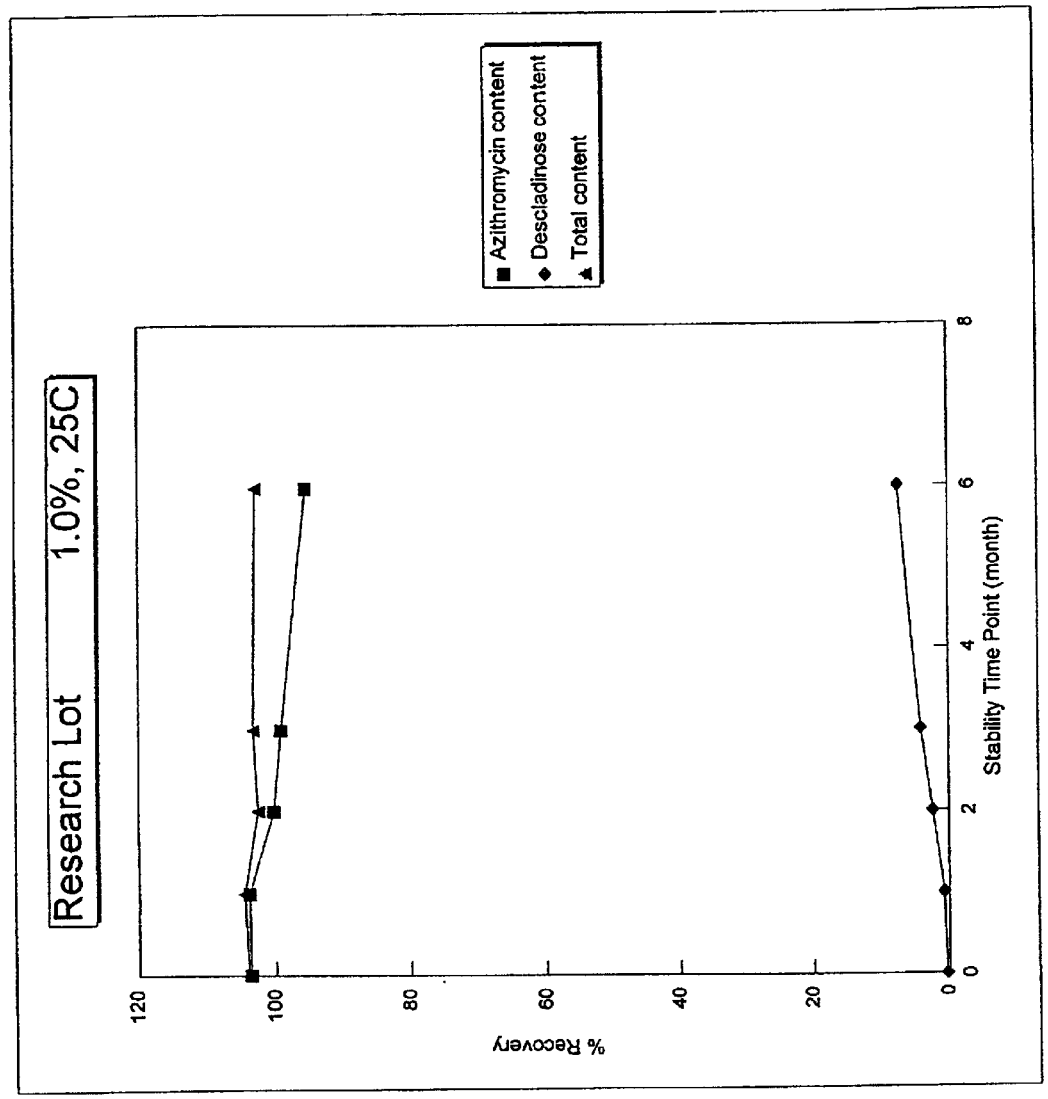
FIG. 11 is a stability graph showing the stability of a Research Lot 1.0%, at 25° C.
Figure 12:
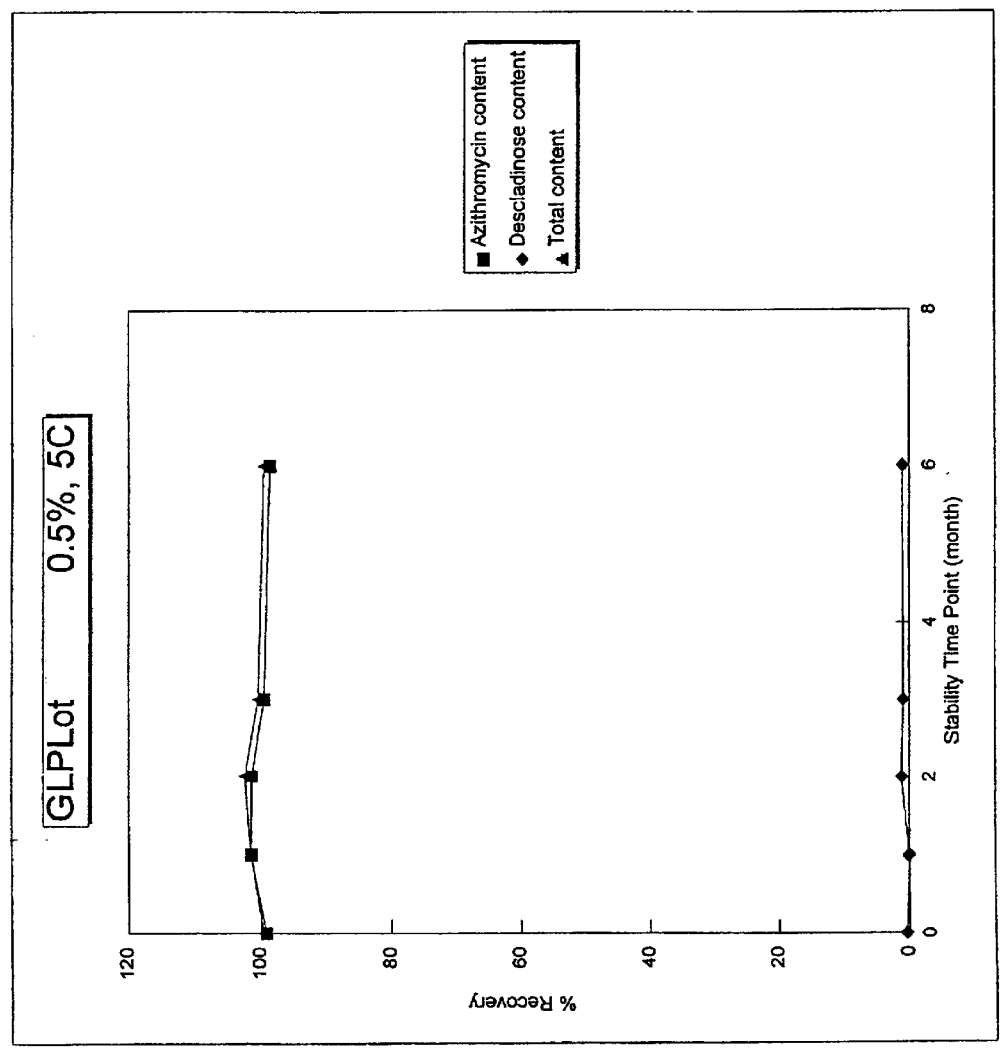
FIG. 12 is a stability graph showing the stability of a GLP Lot 0.5%, at 5° C.
Figure 13:
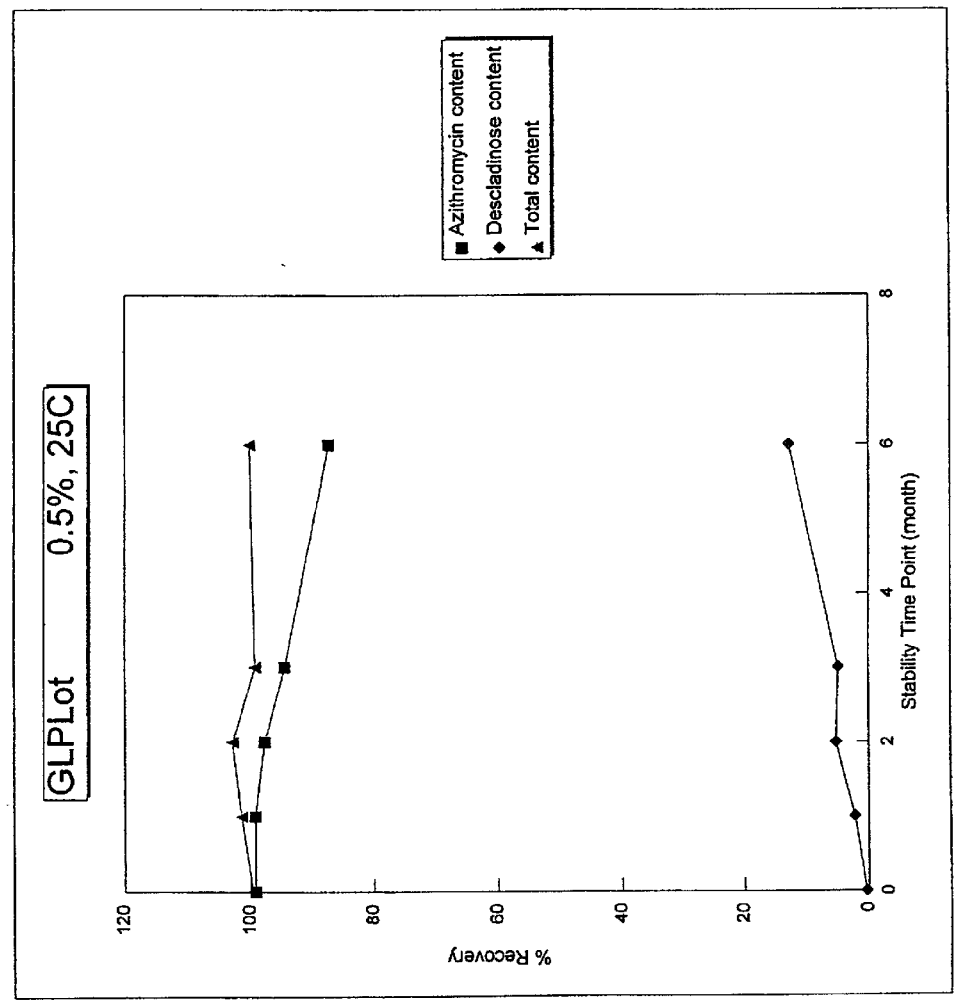
FIG. 13 is a stability graph showing the stability of a GLP Lot 0.5%, at 25° C.
Figure 14:
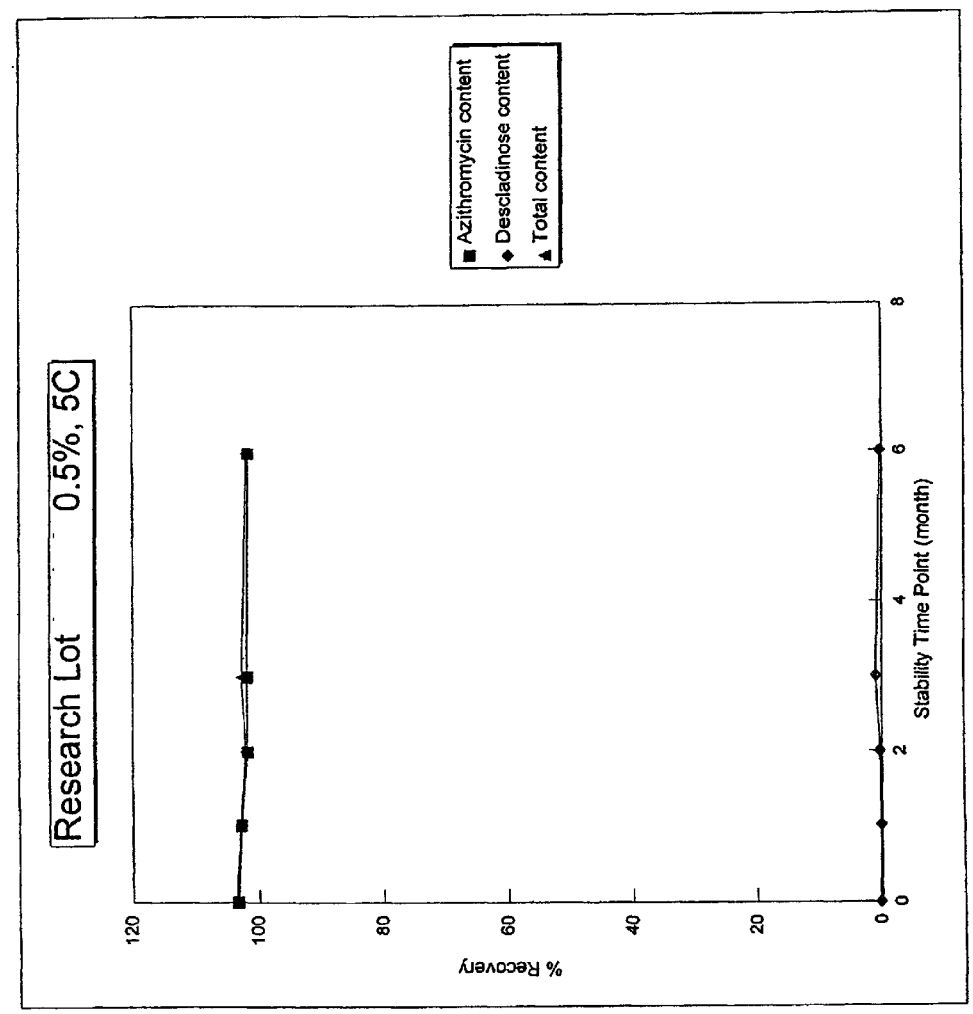
FIG. 14 is a stability graph showing the stability of a Research Lot 0.5%, at 5° C.
Figure 15:
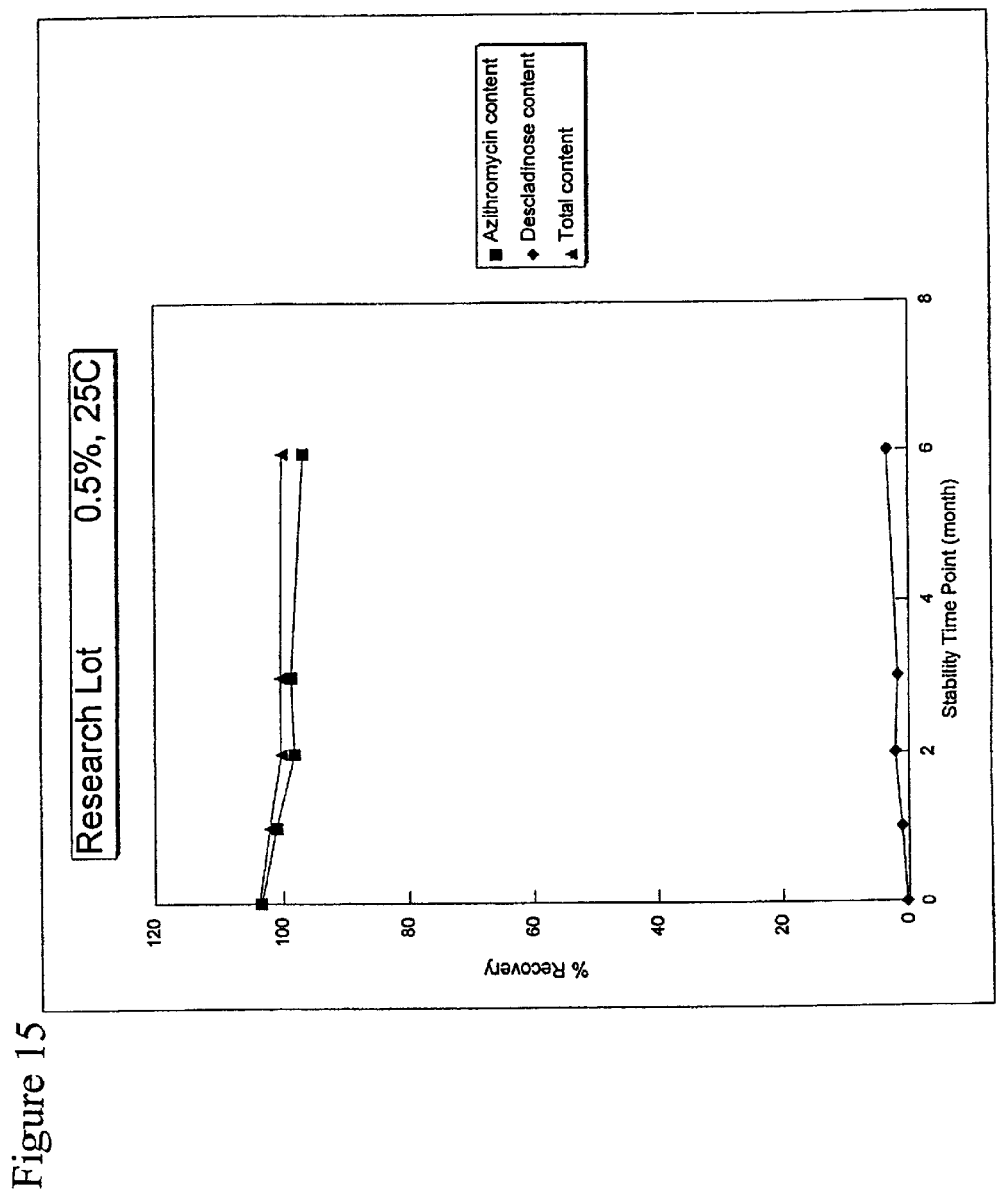
FIG. 15 is a stability graph showing the stability of a Research Lot 0.5%, at 25° C.

The azithromycin content is adjusted to 100% weight content based on the content of azithromycin determined by liquid chromatography. Impurities found to be present at t=0 remain constant at an initial level throughout the duration of the experiment. The azithromycin degradation product, descladinose, increases with time, dependent of temperature, independent of impurities. FIG. 7 depicts the pH Stability of ISV-401 at 40° C. The initial specifications for azithromycin and pH are 95–105% and a pH of 6.3±0.3 for ISV-401 DuraSite Formulation. The specifications during the shelf life for azithromycin and pH are 90–110% and a pH of 6.3±0.5 for ISV-401 DuraSite Formulation.

EXAMPLE 20

Stability Graphs

The change in azithromycin content, within the ISV-401 product formulations, over a 6 month period, are measured at 5° C. and 25° C. as measured by high performance liquid chromatography (HPLC). The graphs in FIGS. 8–15 depict stabliity data for four different lots of ISV-401 at 5° C. and 25° C.:

1.0% azithromycin ISV-401
0.5% azithromycin ISV-401

The major degradation product is determined to be descladinose-azithromycin by LC-MS/MS. The data evidences the stabilty of ISV-401 throughout 6 months of storage at 5° C. and that storage under these conditions results in a minimal change in the content of either azithromycin or the major degradation product. Storage at 25° C. effects a significant decrease in azithromycin content with a nearly identical increase in the content of the major degradation compound (near mass balance) through 6 months of storage.

Tables 6–13 (below) present data corresponding to FIGS. 8–15 respectively.

TABLE 4

GLP Lot 1.0%, 5° C.

| Time point (month) | AZ % recovery | Descladinose % recovery | Total % recovery |
|---|---|---|---|
| 0 | 98.51 | 0.36 | 98.87 |
| 1 | 99.77 | 0.00 | 99.77 |
| 2 | 100.35 | 0.94 | 101.29 |
| 3 | 100.48 | 0.74 | 101.21 |
| 6 | 99.20 | 0.56 | 99.76 |

TABLE 5

GLP Lot 1.0%, 25° C.

| Time point (month) | AZ % recovery | Descladinose % recovery | Total % recovery |
|---|---|---|---|
| 0 | 98.51 | 0.36 | 98.87 |
| 1 | 98.17 | 1.19 | 99.35 |
| 2 | 97.46 | 3.12 | 100.58 |
| 3 | 96.13 | 2.81 | 98.94 |
| 6 | 92.46 | 7.87 | 100.33 |

TABLE 6

Research Lot 1.0%, 5° C.

| Time point (month) | AZ % recovery | Descladinose % recovery | Total % recovery |
|---|---|---|---|
| 0 | 103.65 | 0.32 | 103.97 |
| 1 | 104.08 | 0.11 | 104.19 |
| 2 | 104.19 | 0.39 | 104.57 |
| 3 | 103.93 | 0.89 | 104.82 |
| 6 | 103.98 | 0.18 | 104.16 |

TABLE 7

Research Lot 1.0%, 25° C.

| Time point (month) | AZ % recovery | Descladinose % recovery | Total % recovery |
|---|---|---|---|
| 0 | 103.65 | 0.32 | 103.97 |
| 1 | 103.89 | 0.73 | 104.61 |
| 2 | 100.22 | 2.33 | 102.55 |
| 3 | 99.20 | 4.06 | 103.25 |
| 6 | 95.59 | 7.29 | 102.88 |

TABLE 8

GLP Lot 0.5%, 5° C.

| Time point (month) | AZ % recovery | Descladinose % recovery | Total % recovery |
|---|---|---|---|
| 0 | 99.23 | 0.38 | 99.61 |
| 1 | 101.50 | 0.00 | 101.50 |
| 2 | 101.34 | 1.10 | 102.44 |
| 3 | 99.52 | 0.89 | 100.41 |
| 6 | 98.62 | 0.96 | 99.58 |

TABLE 9

GLP Lot 0.5%, 25° C.

| Time point (month) | AZ % recovery | Descladinose % recovery | Total % recovery |
|---|---|---|---|
| 0 | 99.23 | 0.38 | 99.61 |
| 1 | 99.23 | 2.20 | 101.43 |
| 2 | 97.63 | 5.25 | 102.88 |
| 3 | 94.34 | 4.87 | 99.21 |
| 6 | 87.33 | 12.77 | 100.10 |

TABLE 10

Research Lot 0.5%, 5° C.

| Time point (month) | AZ % recovery | Descladinose % recovery | Total % recovery |
|---|---|---|---|
| 0 | 103.46 | 0.29 | 103.75 |
| 1 | 102.85 | 0.18 | 103.03 |
| 2 | 101.77 | 0.28 | 102.05 |
| 3 | 101.85 | 0.93 | 102.78 |
| 6 | 101.68 | 0.28 | 101.96 |

TABLE 11

Research Lot 0.5%, 25° C.

| Time point (month) | AZ % recovery | Descladinose % recovery | Total % recovery |
|---|---|---|---|
| 0 | 103.46 | 0.29 | 103.75 |
| 1 | 101.05 | 1.08 | 102.13 |
| 2 | 98.15 | 2.11 | 100.26 |
| 3 | 98.72 | 1.70 | 100.42 |
| 6 | 96.77 | 3.36 | 100.13 |

EXAMPLE 21

Stability Analysis of ISV-401

Four lots of ISV-401(1.0% azithromycin, and 0.5% azithromycin) are subject to stability testing at 5° C. and 25° C. over a six month time course. At the indicted intervals, the following parameters are accessed: benzalkonium chloride content (BAK), viscosity, osmolality, pH, color/clarity, sterility, azithromycin content and impurity content. The results are shown in tables 12–15.

TABLE 12

Stability Table for Azithromycin/DuraSite GLP Lot
Product: Azithromycin 1.0% (w/w)    Lot No.:
Packaging: Wheaton, Boston Round Bottle, 7.5 mL, White, LDPE

| Storage Condition | Time | Test Method | BAK (% w/w) | Viscosity (cP) | Osmolality (mOsm/kg) | pH | Color/Clarity | Sterility | Azithromycin (% w/w) | Impurity C (% w/w) |
|---|---|---|---|---|---|---|---|---|---|---|
| | | Method | IPEI125.00 | IPEI124.01 | TM414.02 | IPGM213.00 | IPEI0118.02 | USP | IPEI126.00 | IPGM126.00 |
| | | Specification | 0.008–0.012 | 1500 + 800 | 275 + 35 | 6.3 + 0.5 | Off-white to slightly yellow | Pass | 0.90–1.10 | |
| Initial (T₀) | 0 mo | | 0.0099, 0.0099 | 1275, 1275 | 254, 254, 254 | 6.21 | Off-white, N8.75 Translucent | Pass | 0.9839, 0.9862 | 0.0042, 0.0030 |
| 5° C. | 1 mo | | 0.00096, 0.0.0098 | 1229, 1236 | 253, 253, 253 | 6.21, 6.21 | Off-white, N8.75 Translucent | | 0.9989, 0.9965 | |
| | 2 mo | | 0.0098, 0.0097 | 1224, 1298 | 254, 254, 254 | 6.22 | Off-white, N8.75 Translucent | | 1.0030, 1.0039 | 0.0089, 0.0099 |
| | 3 mo | | 0.0098, 0.0098 | 1321, 1267 | 254, 254, 253 | 6.24, 6.23 | Off-white, N8.5 Translucent | | 0.9989, 1.0106 | 0.0076, 0.0071 |
| | 6 mo | | 0.0099, 0.0099 | 1413, 1390 | 254, 254, 255 | 6.27 | Off-white, N8.5 Translucent | | 0.9877, 0.9962 | 0.0781, 0.0793 |
| 25° C. | 1 mo | | 0.0096, 0.0098 | 1298, 1329 | 255, 254, 254 | 6.21, 6.21 | Off-white, N8.75 Translucent | | 0.9855, 0.9778 | 0.0129, 0.0108 |
| | 2 mo | | 0.0098, 0.0098 | 1321, 1290 | 256, 255, 256 | 6.22 | Off-white, N8.75 Translucent | | 0.9733, 0.9759 | 0.0316, 0.0308 |
| | 3 mo | | 0.0099, 0.0099 | 1428, 1421 1252, 1229 | 256, 256, 256 | 6.23, 6.24 | Off-white, N8.5 Translucent | | 0.9634, 0.9592 | 0.0284, 0.0277 |
| | 6 mo | | 0.0099, 0.0100 | 1428, 1459 | 258, 259, 259 | 6.27 | Off-white, N8.5 Translucent | | 0.9266, 0.9226 | 0.0781, 0.0793 |

TABLE 13

Stability Table for Azithromycin/DuraSite Research Lot
Product: Azithromycin 1.0% (w/w)    Lot No.:
Packaging: Wheaton, Boston Round Bottle, 7.5 mL, White, LDPE

| Storage Condition | Time | Test Method | Aithromycin (% w/w) | Impurity C (% w/w) | BAK (% w/w) | Viscosity (cP) | Osmolality (mOsm/kg) | pH | Color/Clarity |
|---|---|---|---|---|---|---|---|---|---|
| | | Method | IPEI 126.00 | IPEI125.00 | IPEI 124.01 | IPEI 124.01 | TM414.02 | IPGM 213.00 | IPE1018 |

TABLE 13-continued

Stability Table for Azithromycin/DuraSite Research Lot
Product: Azithromycin 1.0% (w/w)   Lot No.:
Packaging: Wheaton, Boston Round Bottle, 7.5 mL, White, LDPE

|  | Test | Aithromycin (% w/w) | Impurity C (% w/w) | BAK (% w/w) | Viscosity (cP) | Osmolality (mOsm/kg) | pH | Color/Clarity |
|---|---|---|---|---|---|---|---|---|
|  | Specification | 0.90–1.10 | Record | 0.008–0.012 | 1500 + 800 | 275 + 35 | 6.3 + 0.5 | Off-white to slightly yellow/Translucent |
| Initial (T$_0$) | 0 mo | 1.0404, 1.0326 | 0.0032, 0.0031 | 0.0100, 0.0101 | 1467, 1429 | 259, 259, 260 | 6.23 | Off-white N8.25 Translucent |
| 5° C. | 1 mo | 1.0372, 1.0443 | 0.0022 | 0.0101, 0.0101 | 1705, 1690 | 262, 262, 263 | 6.26 | Off-white N8.75 Translucent |
|  | 2 mo | 1.0413, 1.0424 | 0.0036, 0.0041 | 0.0099, 0.0099 | 1574, 1628 | 261, 260, 260 | 6.21, 6.21 | Off-white N8.75 Translucent |
|  | 3 mo | 1.0439, 1.0346 | 0.0093, 0.0085 | 0.0100, 0.0100 | 1557, 1557 | 262, 261, 262 | 6.24 | Off-white N8.75 Translucent |
|  | 6 mo | 1.0386, 1.0409 | 0.0036 | 0.0100, 0.0100 | 1659, 1620 | 262, 263, 263 | 6.18 | Off-white N8.75 Translucent |
| 25° C. | 1 mo | 1.0383, 1.0394 | 0.0064, 0.0081 | 0.0100, 0.0100 | 1697, 1682 | 262, 262, 263 | 6.23 | Off-white N8.75 Translucent |
|  | 2 mo | 1.0049, 0.9994 | 0.0225, 0.0241 | 0.0099, 0.0098 | 1667, 1651 | 262, 262, 262 | 6.21, 6.21 | Off-white N8.75 Translucent |
|  | 3 mo | 0.9946, 0.9893 | 0.0403, 0.0408 | 0.0100, 0.0100 | 1736, 1736 | 263, 263, 263 | 6.22 | Off-white N8.75 Translucent |
|  | 6 mo | 0.9537, 0.9580 | 0.0735, 0.0723 | 0.0099, 0.0099 | 1843, 1789, 1843 | 264, 264, 265 | 6.19 | Off-white N8.75 Translucent |

TABLE 14

Stability Table for Azithromycin/DuraSite GLP Lot
Product: Azithromycin 0.5% (w/w)   Lot No.:
Packaging: Wheaton, Boston Round Bottle, 7.5 mL, White, LDPE

|  | Test | BAK (% w/w) | Viscosity (cP) | Osmolality (mOsm/kg) | pH | Color/Clarity | Sterility | Azithromycin (% w/w) | Impurity C (% w/w) |
|---|---|---|---|---|---|---|---|---|---|
| Storage Condition | Time Method | IPEI125.00 | IPEI124.01 | TM414.02 | IPGM 213.00 | IPEI018.02 | USP | IPEI126.00 | IPEI126.00 |
|  | Specification | 0.008–0.012 | 1500 + 800 | 275 + 35 | 6.3 + 0.5 | Off-white to slightly yellow | Pass | 0.45–0.55 |  |
| Initial (T$_0$) | 0 mo | 0.0098, 0.0097 | 1175, 1175 | 253, 252, 252 | 6.02 | Off-white, N8.75 Translucent | Pass | 0.4993, 0.4930 | 0.0019, 0.0019 |
| 5° C. | 1 mo | 0.0095, 0.0095 | 1252, 1267 | 252, 251, 252 | 5.95, 5.95 | Off-white, N8.75 Translucent |  | 0.5058, 0.5092 |  |
|  | 2 mo | 0.0096, 0.0095 | 1183, 1229 | 253, 253, 253 | 5.98 | Off-white, N8.75 Translucent |  | 0.5081, 0.5053 | 0.0054, 0.0056 |
|  | 3 mo | 0.0096, 0.0096 | 1183, 1213 | 253, 253, 253 | 6.01, 6.01 | Off-white, N8.5 Translucent |  | 0.4942, 0.5010 | 0.0042, 0.0047 |
|  | 6 mo | 0.0097, 0.0097 | 1275, 1283 | 253, 253, 253 | 6.05 | Off-white, N8.5 Translucent |  | 0.4910, 0.4952 | 0.0053, 0.0043 |
| 25° C. | 1 mo | 0.0095, 0.0096 | 1221, 1283 | 253, 252, 253 | 5.96, 5.96 | Off-white, N8.75 Translucent |  | 0.4931, 0.4992 | 0.0108, 0.0112 |
|  | 2 mo | 0.0098, 0.0097 | 1244, 1221 | 254, 254, 254 | 5.98 | Off-white, N8.75 Translucent |  | 0.4883, 0.4880 | 0.0266, 0.0259 |
|  | 3 mo | 0.0097, 0.0097 | 1290, 1290 | 254, 254, 254 | 5.99, 5.98 | Off-white, N8.5 Translucent |  | 0.4715, 0.4719 | 0.0240, 0.0247 |
|  | 6 mo | 0.0099, 0.0098 | 1382, 1375 | 257, 256, 257 | 6.04 | Off-white, N8.5 Translucent |  | 0.4367, 0.4366 | 0.0630, 0.0647 |

TABLE 15

Stability Table for Azithromycin/DuraSite Research Lot
Product: Azithromycin 0.5% (w/w)   Lot No.:
Packaging: Wheaton, Boston Round Bottle, 7.5 mL, White, LDPE

|  | Test | Azithromycin (% w/w) | Impurity C (% w/w) | BAK (% w/w) | Viscosity (cP) | Osmolality (mOsm/kg) | pH | Color/Clarity |
|---|---|---|---|---|---|---|---|---|
| Storage Condition | Time Method | IPEI126.00 |  | IPEI125.00 | IPEI124.01 | TM414.02 | IPGM 213.00 | IPEI018 |
|  | Specification | 0.45–0.55 | Record | 0.008–0.012 | 1500 ± 800 | 275 ± 35 | 6.3 ± 0.5 | Off-white to slightly yellow /Translucent |

TABLE 15-continued

Stability Table for Azithromycin/DuraSite Research Lot
Product: Azithromycin 0.5% (w/w)   Lot No.:
Packaging: Wheaton, Boston Round Bottle, 7.5 mL, White, LDPE

| | Test | Azithromycin (% w/w) | Impurity C (% w/w) | BAK (% w/w) | Viscosity (cP) | Osmolality (mOsm/kg) | pH | Color/Clarity |
|---|---|---|---|---|---|---|---|---|
| Initial (T₀) | 0 mo | 0.5200, 0.5146 | 0.0013, 0.0016 | 0.0102, 0.0101 | 1636, 1644 | 249, 249, 249 | | Off-white N8.25 Translucent |
| 5° C. | 1 mo | 0.5158, 0.5177 | 0.0010, 0.0008 | 0.0100, 0.0100 | 1843, 1825 | 249, 250, 250 | 6.47 | Off-white N8.75 Translucent |
| | 2 mo | 0.5070, 0.5107 | 0.0016, 0.0012 | 0.0098, 0.0098 | 1743, 1728 | 248, 247, 247 | 6.49, 6.49 | Off-white N8.75 Translucent |
| | 3 mo | 0.5089, 0.5096 | 0.0048, 0.0045 | 0.0100, 0.0100 | 1759, 1728 | 250, 250, 249 | 6.54 | Off-white N8.75 Translucent |
| | 6 mo | 0.5054, 0.5114 | 0.0028 | 0.0099, 0.0099 | 1997, 1774, 1920, 1905 | 250, 250, 250 | 6.51 | Off-white N8.75 Translucent |
| 25° C. | 1 mo | 0.5043, 0.5062 | 0.0052, 0.0056 | 0.0098, 0.0098 | 1743, 1720 | 248, 248, 248 | 6.50, 6.50 | Off-white N8.75 Translucent |
| | 2 mo | 0.4912, 0.4903 | 0.0107, 0.0104 | 0.0102, 0.0102 | 1782, 1789 | 252, 252, 253 | 6.54 | Off-white N8.75 Translucent |
| | 3 mo | 0.4939, 0.4933 | 0.0083, 0.0087 | 0.0099, 0.0099 | 1797, 1797 | 251, 250, 250 | 6.54, 6.58 | Off-white N8.5 Translucent |
| | 6 mo | 0.4860 0.4817 | 0.0170, 0.0166 | 0.0102, 0.0101 | 1743, 1743 | 253, 253, 253 | 6.58 | Off-white N8.5 Translucent |

The above discussion of this invention is directed primarily to preferred embodiments and practices thereof. It will be readily apparent to those skilled in the art that further changes and modifications in actual implementation of the concepts described herein can easily be made or may be learned by practice of the invention, without departing from the spirit and scope of the invention as defined by the following claims.

This application incorporates by reference the entire contents of each United States patent, patent application, and reference discussed herein.

We claim:

1. A composition comprising water, a polymeric suspending agent and an azalide antibiotic, wherein said composition has a pH of about 6.0 to 6.6.

2. The composition of claim 1, wherein said composition is an ophthalmic composition.

3. The composition of claim 2, wherein said polymeric suspending agent is a water-swellable water-insoluble crosslinked carboxy-vinyl polymer.

4. The composition of claim 3, wherein said polymer comprises at least 90% acrylic acid monomers and about 0.1% to about 5.0% of a difunctional crosslinking agent, wherein said polymeric suspending agent is contained in an amount of about 0.5% to about 1.2%.

5. The composition of claim 1, wherein said composition is incorporated into a formulation administerable in a depot format.

6. The composition of claim 5, wherein said depot contains sufficient azalide antibiotic to maintain the azalide antibiotic above the $MIC_{50}$ for at least about 12 hours after administration.

7. The composition of claim 1, wherein said azalide antibiotic is azithromycin.

8. The composition of claim 1, wherein said azalide antibiotic has a formula of:

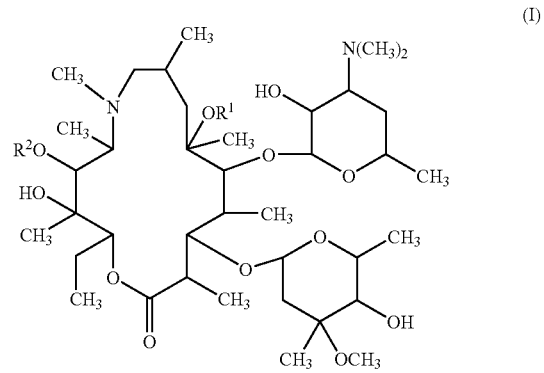

(I)

wherein $R^1$ and $R^2$ each independently represent a hydrogen atom or a methyl group.

9. The composition of claim 1, wherein said azalide antibiotic is present at a concentration of about 0.1% to about 10.0%.

10. The composition of claim 1, wherein said composition has a pH of about 6.0 to about 6.5.

11. The composition of claim 1, wherein said composition has a pH of about 6.2 to about 6.4.

12. The composition of claim 1, wherein said composition has a pH of about 6.3.

13. A composition comprising water, an azalide antibiotic, and one or more agents selected from the group consisting of: a buffering agent, an osmolarity adjusting agent, disodium EDTA, a polymeric suspending agent, a water-swellable water-insoluble crosslinked carboxy-vinyl polymer that comprises at least 90% acrylic acid monomers and about 0.1% to about 5.0% crosslinking agent, and an additional medicament selected from the group consisting of an antibiotic, an antiviral, an antifungal, an anesthetic, an anti-inflammatory agent, and an anti-allergic agent, wherein said composition has a pH of about 6.0 to 6.6.

14. The composition of claim 13, wherein the additional medicament is selected from the group consisting of amikacin, gentamycin, tobramycin, streptomycin, netilmycin, kanamycin, ciprofloxacin, norfloxacin, ofloxacin, trovafloxacin, lomefloxacin, levofloxacin, enoxacin, sulfonamides, polymyxin, chloramphenicol, neomycin, paramomomycin, colistimethate, bacitracin, vancomycin, tetracyclines, rifampins, cycloserine, beta-lactams, cephalosporins, amphotericins, fluconazole, flucytosine, natamycin, miconazole, ketoconazole, corticosteroids, diclofenac, flurbiprofen, ketorolac, suprofen, comolyn, lodoxamide, levocabastin, naphazoling, antazoline, and pheniramimane.

15. A solid, semi-solid, powdered, or lyophilized composition comprising an azalide antibiotic and a polymeric suspending agent, which upon addition of water produces an aqueous formulation having a pH from about 6.0 to about 6.6.

16. The composition according to claim 15, wherein said polymeric suspending agent is a lightly crosslinked carboxy vinyl polymer.

17. A method of preparing a stable azalide antibiotic composition for medicinal use, comprising the steps of:
    (a) dispersing or solubilizing an azalide antibiotic and a polymeric suspending agent in an aqueous medium having a pH less than about 5.0;
    (b) adding a base to the composition formed in step (a);
    (c) adding water to the solution formed in step (b); and
    (d) adjusting the solution formed in step (c) to a pH of about 6.0 to about 6.6.

18. The method as in claim 17, wherein the aqueous medium employed in step (a) is a citric acid buffer or solution, and the base in step (b) is sodium citrate.

19. The method of claim 17, wherein said pH is adjusted by adding sodium hydroxide in step (b) or step (d).

20. The method of claim 17, wherein said composition has been formulated for ocular administration and said polymeric suspending agent is a water-swellable water-insoluble crosslinked carboxy-vinyl polymer; wherein said polymer comprises at least 90% acrylic acid monomers and about 0.1% to about 5.0% of a difunctional crosslinking agent and said pH in step (d) is from about 6.2 to about 6.4; said composition having an initial viscosity which increases when the pH of the composition rises to at least about 7.0 upon administration to a target tissue.

21. The method of claim 17, wherein said composition is a ocular composition to be administered as a depot, and wherein said composition contains sufficient azalide antibiotic to provide a sustained release of the administration of the antibiotic to the target tissue for least about 12 hours.

22. The method of claim 17, further comprising the step of (e) adding an agent to adjust osmolarity.

23. A method of treating a patient infected with a bacterial infection comprising administering a composition comprising an azalide antibiotic formulation and a polymeric suspending agent to a subject in need thereof in an antibacterial effective amount, wherein said composition has a pH from about 6.0 to about 6.6.

24. The method of claim 23, wherein said pH is from about 6.0 to about 6.5.

25. The method of claim 23, wherein said pH is from about 6.2 to about 6.4.

26. The method of claim 23, wherein said pH is about 6.3.

27. A method of treating a patient infected with a bacterial infection comprising administering a composition comprising an azalide antibiotic formulation to an eye of a subject in need thereof in an antibacterial effective amount, wherein said composition has a pH from about 6.0 to about 6.6.

28. The method of 27, wherein said composition is injected into the eye.

29. The method of 23, wherein said composition is topically applied to the eye.

30. The method of claim 29, wherein said polymeric suspending agent is a water-swellable water-insoluble crosslinked carboxy-vinyl polymer, and wherein said carboxy-vinyl polymer comprises at least 90% acrylic acid monomers and about 0.1% to about 5% crosslinking agent and a difunctional crosslinking agent.

31. The method of claim 27, wherein said composition is to be administered as a depot, and wherein said composition contains sufficient azalide antibiotic to provide a sustained release of the administration of the antibiotic to the target tissue for at least about 12 hours.

32. The method of claim 27, wherein said azalide antibiotic is azithromycin.

33. The method of claim 27, wherein said azalide antibiotic has a formula of:

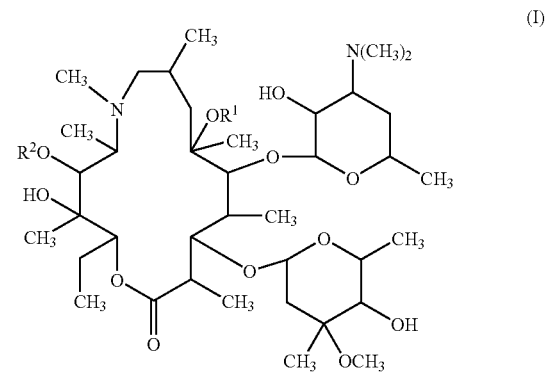

(I)

wherein $R^1$ and $R^2$ each independently represent a hydrogen atom or a methyl group.

34. The method of claim 23, wherein said composition further comprises an agent to adjust osmolarity.

35. The method of claim 23, wherein said composition further comprises one or more additional medicaments.

36. The composition of claim 2, wherein said polymer comprises at least 90% acrylic acid monomers and about 0.1% to about 5.0% of a difunctional crosslinking agent, wherein said polymeric suspending agent is contained in an amount of about 0.5% to about 1.2%.

37. The composition of claim 1, further comprising one or more agents selected from the group consisting of: a solubilizing agent, a buffering agent, an osmolarity adjusting agent, a chelating agent, disodium EDTA, a polymeric suspending agent, a water-swellable water-insoluble crosslinked carboxy-vinyl polymer that comprises at least 90% acrylic acid monomers and about 0.1% to about 5.0% crosslinking agent, and an additional medicament selected from the group consisting of an antibiotic, an antiviral, an antifungal, an anesthetic, an anti-inflammatory agent, and an anti-allergic agents.

38. The composition of claim 1, wherein said azalide antibiotic is present at a concentration of about 0.1% to about 0.5%.

39. The method of treating a patient of claim 23, wherein said administering is one or two doses of said composition per day for one to three days.

40. The method of treating a patient of claim 23, wherein said administering is one or two doses of said composition per day for at least six days.

41. The method of treating a patient of claim 23, wherein said administering is one or two doses of said composition per day for six to fourteen days.

42. The method of treating a patient of claim 27, wherein said administering is one or two doses of said composition per day for one to three days.

43. The method of treating a patient of claim 27, wherein said administering is one or two doses of said composition per day for at least six days.

44. The method of treating a patient of claim 27, wherein said administering is one or two doses of said composition per day for six to fourteen days.

* * * * *